(12) United States Patent
Thayer et al.

(10) Patent No.: US 7,229,839 B2
(45) Date of Patent: Jun. 12, 2007

(54) BIDIRECTIONAL LATERAL FLOW TEST STRIP AND METHOD

(75) Inventors: Richard M. Thayer, Alamo, CA (US); Alan J. Polito, Danville, CA (US); Robert K. Dinello, Hayward, CA (US); George H. Sierra, Concord, CA (US); Henry J. Wieck, Plainsboro, NJ (US)

(73) Assignee: Relia Diagnostic Systems, LLC, San Francisco, CA (US)

( * ) Notice: Subject to any disclaimer, the term of this patent is extended or adjusted under 35 U.S.C. 154(b) by 784 days.

(21) Appl. No.: 10/346,683

(22) Filed: Jan. 17, 2003

(65) Prior Publication Data

US 2003/0157729 A1 Aug. 21, 2003

Related U.S. Application Data

(63) Continuation of application No. 09/332,933, filed on Jun. 14, 1999, now Pat. No. 6,528,323.

(51) Int. Cl.
*G01N 33/53* (2006.01)

(52) U.S. Cl. ..................... 436/518; 436/514; 436/164; 436/165; 436/169; 436/528; 436/530; 436/805; 436/810; 436/811; 436/817; 435/287.6; 435/970; 435/810; 435/974; 435/975

(58) Field of Classification Search ............... 436/518, 436/164, 165, 169, 514, 528, 530, 805, 807, 436/808, 810, 811, 817; 435/287.6, 970, 435/810, 974, 975
See application file for complete search history.

(56) References Cited

U.S. PATENT DOCUMENTS 4,626,684 A 12/1986 Landa (Continued)

FOREIGN PATENT DOCUMENTS

EP 0 322 340 A2 6/1989

(Continued)

OTHER PUBLICATIONS

Stephenson, "RAMP: a quantitative immunoassay platform takes shape," *IVD Technology* 51, 1998.

(Continued)

*Primary Examiner*—Bao-Thuy L. Nguyen
(74) *Attorney, Agent, or Firm*—Cooley Godward Kronish LLP

(57) ABSTRACT

A test strip adapted to receive a sample and detect an analyte therein is provided. The test strip comprises a sample addition zone to which a sample may be added; an absorbent zone proximal to the sample addition zone; one or more test zones distal to the sample addition zone, at least one of the test zones including a first analyte binding agent immobilized therein which is capable of binding to the analyte to be detected; and a terminal sample flow zone distal to the one or more test zones, the absorbent zone being positioned relative to the sample addition zone and having an absorption capacity relative to the other zones of the test strip such that a distal diffusion front of a sample added to the sample addition zone diffuses from the sample addition zone to a distal diffusion point within the terminal sample flow zone and then reverses direction and diffuses proximal relative to the one or more test zones.

15 Claims, 14 Drawing Sheets

U.S. PATENT DOCUMENTS

| | | |
|---|---|---|
| 4,822,566 A | 4/1989 | Newman |
| 5,028,535 A | 7/1991 | Buechler et al. |
| 5,049,487 A | 9/1991 | Phillips et al. |
| 5,089,391 A | 2/1992 | Buechler et al. |
| 5,232,835 A | 8/1993 | Litman et al. |
| 5,238,652 A | 8/1993 | Sun et al. |
| 5,300,779 A | 4/1994 | Hillman et al. |
| 5,344,754 A | 9/1994 | Zweig |
| 5,356,785 A | 10/1994 | McMahon et al. |
| 5,413,939 A | 5/1995 | Gustafson et al. |
| 5,418,143 A | 5/1995 | Zweig |
| 5,458,852 A | 10/1995 | Buechler |
| 5,468,648 A | 11/1995 | Chandler |
| 5,554,531 A | 9/1996 | Zweig |
| 5,580,794 A | 12/1996 | Allen |
| 5,589,399 A | 12/1996 | Allen et al. |
| 5,650,334 A | 7/1997 | Zuk et al. |
| 5,679,526 A | 10/1997 | Buechler et al. |
| 5,679,579 A | 10/1997 | Gustafson |
| 5,750,333 A | 5/1998 | Clark |
| 5,753,517 A | 5/1998 | Brooks et al. |
| 5,766,875 A | 6/1998 | Hafeman et al. |
| 5,922,615 A | 7/1999 | Nowakowski et al. |
| 5,939,272 A | 8/1999 | Buechler et al. |
| 6,007,999 A | 12/1999 | Clark |
| 6,136,610 A | 10/2000 | Polito et al. |

FOREIGN PATENT DOCUMENTS

| | | |
|---|---|---|
| WO | WO 91/13998 A1 | 9/1991 |
| WO | WO 93/03176 A1 | 2/1993 |
| WO | WO 96/07101 A1 | 3/1996 |
| WO | WO 96/22533 A1 | 7/1996 |
| WO | WO 97/07993 A1 | 3/1997 |
| WO | WO 97/08551 A1 | 3/1997 |
| WO | WO 97/37222 A1 | 10/1997 |
| WO | WO 98/27435 A1 | 6/1998 |
| WO | WO 00/58730 A1 | 10/2000 |

OTHER PUBLICATIONS

Biosite Diagnostics, Inc., Triage Drugs of Abuse Panel, website: www.biosite.com/products/doa/doa.html, retrieved Feb. 23, 1999.

Biosite Diagnostics, Inc., Triage C.Difficile Panel, website: www.biosite.com/products/cdiff/cdifficile.html, retrieved Feb. 23, 1999.

Biosite Diagnostics, Inc., Triage Parasite Panel, website: www.biosite.com/products/parasite/parasite.html, retrieved Feb. 23, 1999.

Biosite Diagnostics, Inc., Triage Cardiac System, website: www.biosite.com/cardiac/cardsystem.html, retrieved Feb. 23, 1999.

| TIME AFTER SOLVENT MEETS LINE | 50m1 (RI) | 45m1 (RI) | 40m1 (RI) | 35m1 (RI) | 32.5m1 (RI) |
|---|---|---|---|---|---|
| 0 MIN. | 3.04 | 3.27 | 2.70 | 2.28 | 1.81 |
| 5 MIN. | 3.88 | 3.16 | 2.99 | 2.63 | 1.77 |
| 15 MIN. | NT | 3.03 | 2.92 | 2.44 | 2.15 |

SAMPLE VOLUME

40○1 ± 5○1 (CV = 12.5%)

| | |
|---|---|
| AVG. | 2.82 |
| STD. DEV. | .333 |
| %CV | 11.8 |

FIG. 8

| SAMPLE | Hc (Dr) | Lc (Dr) | SPECIMEN (Dr) | Hc/Lc | RI |
|---|---|---|---|---|---|
| HSV-2 POS | | | | | |
| 92 | 0.1532 | 0.0256 | 0.0148 | 5.991 | 0.58 |
| 85 | 0.2380 | 0.0426 | 0.0952 | 5.586 | 1.54 |
| 98 | 0.1949 | 0.0294 | 0.1628 | 6.634 | 2.61 |
| 36 | 0.1868 | 0.0284 | 0.0242 | 6.582 | 0.85 |
| 44 | 0.1695 | 0.0283 | 0.1917 | 5.980 | 3.31 |
| 53 | 0.2207 | 0.0719 | 0.1500 | 3.070 | 2.05 |
| 90 | 0.1900 | 0.0317 | 0.2389 | 5.991 | 3.62 |
| 92 | 0.2030 | 0.0352 | 0.0634 | 5.761 | 1.34 |
| 42 | 0.1992 | 0.0423 | 0.0879 | 4.703 | 1.58 |
| 43 | 0.2009 | 0.0601 | 0.1303 | 3.346 | 2.00 |
| HSV-2 NEG | | | | | |
| 855 | 0.2122 | 0.0580 | 0.0004 | 3.658 | 0.01 |
| 861 | 0.1584 | 0.0287 | 0.0001 | 5.526 | 0.00 |
| 857 | 0.1564 | 0.0274 | 0.0000 | 5.700 | 0.00 |
| 853 | 0.1507 | 0.0450 | 0.0000 | 3.348 | 0.00 |
| 862 | 0.1845 | 0.0463 | 0.0000 | 3.983 | 0.00 |
| | | | | | |
| AVG | 0.1879 | 0.0401 | | 5.0573 | |
| STD DEV | 0.0261 | 0.0141 | | 1.2493 | |
| %CV | 13.9 | 35.3 | | 24.7 | |

FIG. 9

| SAMPLE | Hc (Dr) | Lc (Dr) | SPECIMEN (Dr) | Hc/Lc | RI |
|---|---|---|---|---|---|
| *H. pylori* POS | | | | | |
| F-13 | 0.2454 | 0.0545 | 0.1156 | 4.503 | 1.64 |
| F-16 | 0.2114 | 0.0467 | 0.1647 | 4.530 | 2.43 |
| F-18 | 0.1993 | 0.0383 | 0.2158 | 5.205 | 3.20 |
| F-20 | 0.1711 | 0.0293 | 0.1333 | 5.832 | 2.47 |
| 201-04 | 0.2554 | 0.0578 | 0.1440 | 4.423 | 1.87 |
| 201-08 | 0.2119 | 0.0419 | 0.0989 | 5.057 | 1.67 |
| 201-09 | 0.2038 | 0.0306 | 0.2118 | 6.661 | 3.09 |
| 201-12 | 0.2596 | 0.0516 | 0.2229 | 5.030 | 2.65 |
| *H. pylori* NEG | | | | | |
| 0863 | 0.2214 | 0.0627 | 0.0741 | 3.531 | 1.14 |
| 0871 | 0.1880 | 0.0696 | 0.0688 | 2.703 | 0.999 |
| 0862 | 0.2255 | 0.0657 | 0.0451 | 3.435 | 0.69 |
| 0866 | 0.2464 | 0.0776 | 0.0542 | 3.174 | 0.70 |
| 0853 | 0.2631 | 0.0917 | 0.0308 | 2.871 | 0.34 |
| 0870 | 0.2028 | 0.0623 | 0.0354 | 3.257 | 0.57 |
| 0861 | 0.2655 | 0.0723 | 0.0647 | 3.674 | 0.90 |
| 0857 | 0.2052 | 0.0456 | 0.3860 | 4.495 | 0.84 |
| 0855 | 0.2424 | 0.1074 | 0.8720 | 2.258 | 0.81 |
| 0868 | 0.2319 | 0.0491 | 0.0470 | 4.721 | 0.96 |
| AVG | 0.2250 | 0.0586 | | 4.1867 | |
| STD DEV | 0.0277 | 0.0203 | | 1.1578 | |
| %CV | 12.3 | 34.7 | | 27.7 | |

FIG. 10

BIDIRECTIONAL LATERAL FLOW TEST STRIP AND METHOD

This application is a continuation of application Ser. No. 09/332,933, filed Jun. 14, 1999 now U.S. Pat. No. 6,528,323, the entire content of which is hereby incorporated by reference.

BACKGROUND OF THE INVENTION

1. Field of the Invention

The present invention relates to lateral flow test strips and methods of operation for the lateral flow test strips.

2. Description of Related Art

Quantitative analysis of cells and analytes in fluid samples, particularly bodily fluid samples, often provides critical diagnostic and treatment information for physicians and patients. For example, immunological testing methods which take advantage of the high specificity of antigen-antibody reactions, provide one approach to measurement of analytes. Kennedy, D. M. and S. J. Challacombe, eds., ELISA and Other Solid Phase Immunoassays: Theoretical and Practical Aspects, John Wiley and Sons, Chichester (1988). This document and all others cited to herein, are incorporated by reference as if reproduced fully below. Such assays may also find use in various other applications, such as veterinary, food testing, or agricultural applications.

Immunoassays that provide a quantitative measurement of the amount of an analyte in a sample have previously used complex, multi-step procedures and expensive analyzers available only in a laboratory setting.

Immunochromatographic assays, such as those described in GB 2,204,398A; U.S. Pat. Nos. 5,096,837, 5,238,652, and 5,266,497; Birnbaum, S. et al., Analytical Biochem. 206: 168–171 (1992); Roberts, M. A. and R. A. Durst, Analytical Chem. 67:482–491 (1995); and Klimov, A. D. et al., Clinical Chem. 41:1360 (1995), are simpler, yet do not provide a quantitative measurement of an analyte. Instead, these immunochromatographic assays detect the presence (or absence) of an analyte above a defined cutoff level for the test performed. The lack of a quantitative measurement limits the usefulness of these assays.

A variety of disposable diagnostic assay devices have also been developed. Examples of such devices include, but are not limited to Cathey, et al, U.S. Pat. No. 5,660,993; International Publication Number WO 92/12428; Eisinger, et al, U.S. Pat. No. 4,943,522; Campbell, et al, U.S. Pat. No. 4,703,017; Campbell, et al, U.S. Pat. No. 4,743,560; and Brooks, U.S. Pat. No. 5,753,517.

SUMMARY OF THE INVENTION

A test strip is provided which is adapted to receive a sample and detect an analyte therein. According to one embodiment, the test strip comprises a sample addition zone to which a sample may be added; an absorbent zone proximal to the sample addition zone; one or more test zones distal to the sample addition zone, at least one of the test zones including a first analyte binding agent immobilized therein which is capable of binding to the analyte to be detected; and a terminal sample flow zone distal to the one or more test zones, the absorbent zone being positioned relative to the sample addition zone and having an absorption capacity relative to the other zones of the test strip such that a distal diffusion front of a sample added to the sample addition zone diffuses from the sample addition zone to a distal diffusion point within the terminal sample flow zone and then reverses direction and diffuses proximal relative to the one or more test zones.

In another embodiment, a test strip is provided which comprises a sample addition zone to which a sample may be added; an absorbent zone proximal to the sample addition zone; one or more test zones distal to the sample addition zone, at least one of the test zones including a first analyte binding agent immobilized therein which is capable of binding to the analyte to be detected; a terminal sample flow zone distal to the one or more test zones, the absorbent zone being positioned relative to the sample addition zone and having an absorption capacity relative to the other zones of the test strip such that a distal diffusion front of a sample added to the sample addition zone within the predetermined volume range diffuses from the sample addition zone to a distal diffusion point within the terminal sample flow zone and then diffuses proximal relative to the one or more test zones; and a conjugate buffer addition zone distal to the terminal sample flow zone to which a conjugate buffer may be added.

According to the above test strip embodiment, the conjugate buffer addition zone may be positioned relative to the test zones such that conjugate buffer added to the conjugate buffer addition zone at the same time as sample is added to the sample addition zone reaches the distal diffusion point after the distal diffusion front of the sample has diffused to the distal diffusion point and begun diffusing in a proximal direction. The conjugate buffer addition zone may also be positioned relative to the test zones such that conjugate buffer added to the conjugate buffer addition zone at the same time that the sample is added to the sample addition zone reaches the test zones after the distal diffusion front of the sample diffuses proximal relative to the test zones. The conjugate buffer addition zone may also be positioned relative to the test zones such that the conjugate buffer can be added to the test strip before the sample and nevertheless reach the distal diffusion point after the distal diffusion front of the sample has diffused to the distal diffusion zone, reversed direction and begun diffusing in a proximal direction.

According to any of the above test strip embodiments, the test strip may include 1, 2, 3 or more test zones with one or more control binding agents immobilized therein. In one embodiment, the test strip comprises at least a first control zone with a control binding agent immobilized therein. Optionally, the test zones further include a second control zone with a same control binding agent immobilized therein as the first control zone, the first control zone containing a different amount of the control binding agent than the second control zone.

Also according to any of the above test strip embodiments, a second analyte binding agent which is capable of binding to the analyte and diffusing to the one or more test zones may be included on the test strip. Alternatively, the second analyte binding agent may be delivered to the test strip via the conjugate buffer. The second analyte binding agent may bind to components in the sample other than the analyte. Alternatively, the second analyte binding agent may be an agent which does not bind to components in the sample other than the analyte.

In order to facilitate detection, the second analyte binding agent is preferably labeled with a detectable marker. As discussed herein, any of a wide range of detectable markers known in the art may be used. In a preferred embodiment, the second analyte binding agent is attached to a particle which is capable of diffusing to the one or more test zones.

The particle may serve as the detectable marker or may itself be labeled with a detectable marker.

A method is also provided for detecting an analyte in a sample. In one embodiment, the method comprises delivering a sample to a test strip which causes a distal diffusion front of the sample to (a) diffuse in a distal direction to one or more test zones, at least one of the test zones including a first analyte binding agent immobilized therein which binds to analyte in the sample, (b) diffuse to a terminal sample flow zone distal to the one or more test zones, change direction and (c) diffuse to a position proximal to the one or more test zones; delivering a conjugate buffer to the test strip at a position distal to the terminal sample flow zone, delivery of the conjugate buffer causing a second analyte binding agent to diffuse proximally past the terminal sample flow zone to the one or more test zones after the distal diffusion front of the sample diffuses proximal to the one or more test zones, the second analyte binding agent binding to analyte immobilized in the test zones; and detecting the second analyte binding agent immobilized in the test zones.

According to the method, the conjugate buffer may be added to the test strip at a same time as the sample is added to the test strip, before the sample is added to the test strip, or after the sample is added to the test strip. When the sample is added to the test strip relative to the conjugate buffer depends on the time required for the sample to reach the terminal sample flow zone which, in turn, depends on the flow design of the test strip.

Also according to the method, the second analyte binding agent may be contained on the test strip where the conjugate buffer is delivered, delivery of the conjugate buffer causing the diffusion of the second analyte binding agent. Alternatively, the second analyte binding agent is contained on the test strip proximal to where the conjugate buffer is delivered, delivery of the conjugate buffer causing the diffusion of the second analyte binding agent. Delivering the conjugate buffer to the test strip may also include delivering the second analyte binding agent to the test strip within the conjugate buffer.

According to the above method, the test zones may include a first control zone with a control binding agent immobilized therein, delivering the conjugate buffer causing a control agent to diffuse proximally past the terminal sample flow zone to the first control zone and bind to the control binding agent immobilized therein. Alternatively, the test zones may include first and second control zones which each include a different amount of a control binding agent immobilized therein, delivering the conjugate buffer causing a control agent to diffuse proximally past the terminal sample flow zone to the first and second control zones and bind to the control binding agent immobilized therein.

Also according to the above method, detecting the second analyte binding agent may be facilitated by labeling the second analyte binding agent with a detectable marker, detecting the second analyte binding agent including detecting the detectable marker. The second analyte binding agent may be attached to a particle. Detecting the second analyte binding agent may include detecting the particle.

According to any of the above embodiments, the sample delivered to the test strip is preferably within a predetermined volume range that the test strip has been designed to process. The predetermined volume range is preferably between about 10 and 250 µL, preferably between about 20 and 100 µL, more preferably between about 30 and 50 µL, and most preferably between about 35 and 45 µL. When a sample is delivered to the test strip within the predetermined volume range, the terminal sample flow zone may be designed to have a short length from a proximal end to a distal end. For example, when a sample is delivered to the test strip within a range of about 35 and 45 µL, the terminal sample flow zone may have a length from a proximal end to a distal end of between about 1 and 25 mm, more preferably 2 and 15 mm, and most preferably 3 and 10 mm.

Also according to any of the above embodiments, the first analyte binding agent preferably does not bind to components in the sample other than the analyte. Types of molecules that can serve as first analyte binding agents include, but are not limited to antibodies, engineered proteins, peptides, haptens, lysates containing heterogeneous mixtures of antigens having analyte binding sites, ligands and receptors. In one particular embodiment, the first analyte binding agent is an antibody or fragment thereof.

BRIEF DESCRIPTION OF THE DRAWINGS

FIG. 2A illustrates a sample being added to the test strip.

FIG. 2B illustrates the sample flowing within the test strip.

FIG. 2C illustrates the test strip when the sample has flowed a distance within the test strip in the direction opposite an absorbent zone to within a terminal sample flow zone.

FIG. 2D illustrates the test strip where the sample is flowing back toward the absorbent zone.

FIG. 2E illustrates the addition of a buffer to the test strip.

FIG. 2F illustrates the flow of the buffer within the test strip toward the absorbent zone.

FIG. 2G illustrates the flow of the buffer within the test strip past the test zone.

FIG. 2H illustrates the flow of the buffer within the test strip into the absorbent zone.

FIG. 3A illustrates a sample and buffer being added to the test strip.

FIG. 3B illustrates the sample and buffer flowing within the test strip.

FIG. 3C illustrates the test strip when the sample has flowed a distance within the test strip in the direction opposite an absorbent zone to a to within terminal sample flow zone.

FIG. 3D illustrates the test strip where the sample is flowing back toward the absorbent zone.

FIG. 3E illustrates the buffer continuing to flow toward the sample flow.

FIG. 3F illustrates the buffer having flowed past the terminal sample flow zone.

FIG. 3G illustrates the flow of the buffer within the test strip past the test zone.

FIG. 3H illustrates the flow of the buffer within the test strip into the absorbent zone.

FIG. 5A illustrates a cartridge design adapted for the test strip illustrated in FIGS. 2A–2H.

FIG. 5B illustrates a cartridge design adapted for the test strip illustrated in FIGS. 3A–3H where the sample addition zone is positioned an extended distance from the wash buffer addition zone such that the sample and wash buffer can be added at the same time.

FIG. 5C illustrates a cartridge design adapted for the test strip illustrated in FIG. 4 where the sample addition zone is positioned adjacent the wash buffer addition zone, the test zone being positioned an extended distance from the wash buffer addition zone.

FIG. 8 illustrates the results from a ReLIA™ stop flow Herpes 2 assay performed in Example 2.

FIG. 9 illustrates the results from a ReLIA™ stop flow Herpes 2 assay performed in Example 3.

FIG. 10 illustrates the results from a ReLIA™ stop flow *Helicobacter pylori* assay performed in Example 4.

DESCRIPTION OF THE PREFERRED EMBODIMENTS

The present invention relates to a lateral flow test strip which is capable of causing a portion of a sample added to the test strip to flow from a zone where the sample is added across one or more test zones into a terminal sample flow zone and then, independent of any user intervention, reverses direction and flow back across the one or more test zones toward the sample addition zone. Immobilized in at least one of the test zones is a first analyte binding agent which is capable of binding to an analyte in the sample which the test strip is designed to detect. By causing a portion of the sample to flow across the one or more test zones and then independently flow back toward the sample addition zone, the need to wash the one or more test zones prior to contacting the one or more test zones with a second analyte binding agent is eliminated. The need to time when the second analyte binding agent is caused to diffuse to the one or more test zones is also eliminated. As will be discussed herein in greater detail, the self-washing and self-timing features of test strips according to the present invention provides several significant advantages over previous test strips.

The self-washing and self-timing features of test strips according to the present invention is achieved by positioning an absorbent zone relative to the sample addition zone such that when a volume of sample (within a predetermined sample volume range for that test strip) is added to the test strip, the diffusion front of the sample expands across the one or more test zones to a terminal sample flow zone. When the sample reaches the terminal sample flow zone, the absorbent properties of the absorbent zone causes the sample to be drawn backward across the test zones toward the sample addition zone and ultimately into the absorbent zone.

Figure 1:
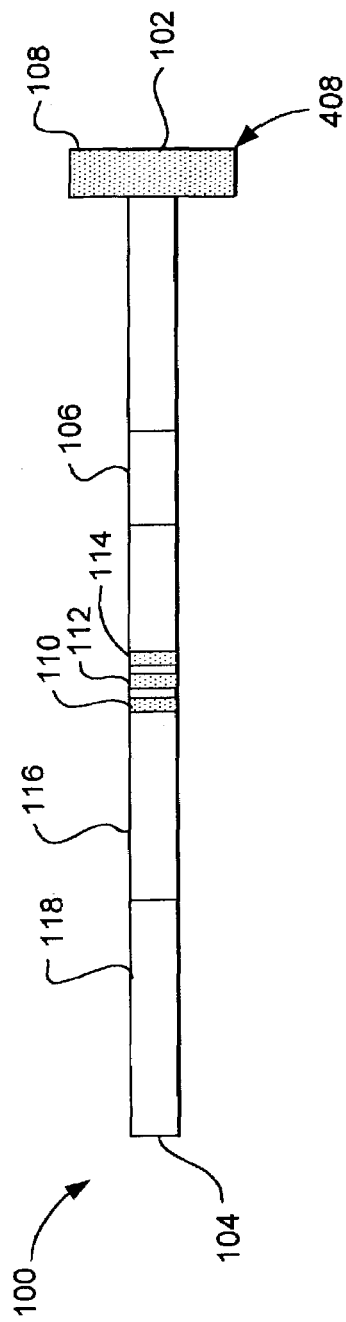
FIG. 1 illustrates a top-down view of an embodiment of a lateral flow test strip according to the present invention.

FIG. 1 illustrates a top-down view of an embodiment of a lateral flow test strip 100 according to the present invention. As illustrated, the test strip 100 has proximal and distal ends 102, 104 respectively and can be divided into several different zones. The test strip includes a sample addition zone 106 where a sample may be added to the test strip 100. An absorbent zone 108 is positioned proximal to the sample addition zone 106. One or more test zones 110, 112, 114 are positioned distal to the sample addition zone 106. The test strip 100 also includes a terminal sample flow zone 116 distal to the one or more test zones 110, 112, 114. Each of the above mentioned zones are in fluid diffusion communication with each other.

As illustrated, the test strip also includes a conjugate buffer addition zone 118 distal to the terminal sample flow zone 116. The conjugate buffer addition zone 118 may be a zone where conjugate buffer may be added to the test strip. Alternatively, the conjugate buffer addition zone 118 may simply correspond to a zone to which conjugate buffer diffuses from a more distal point on the test strip.

Figure 4:
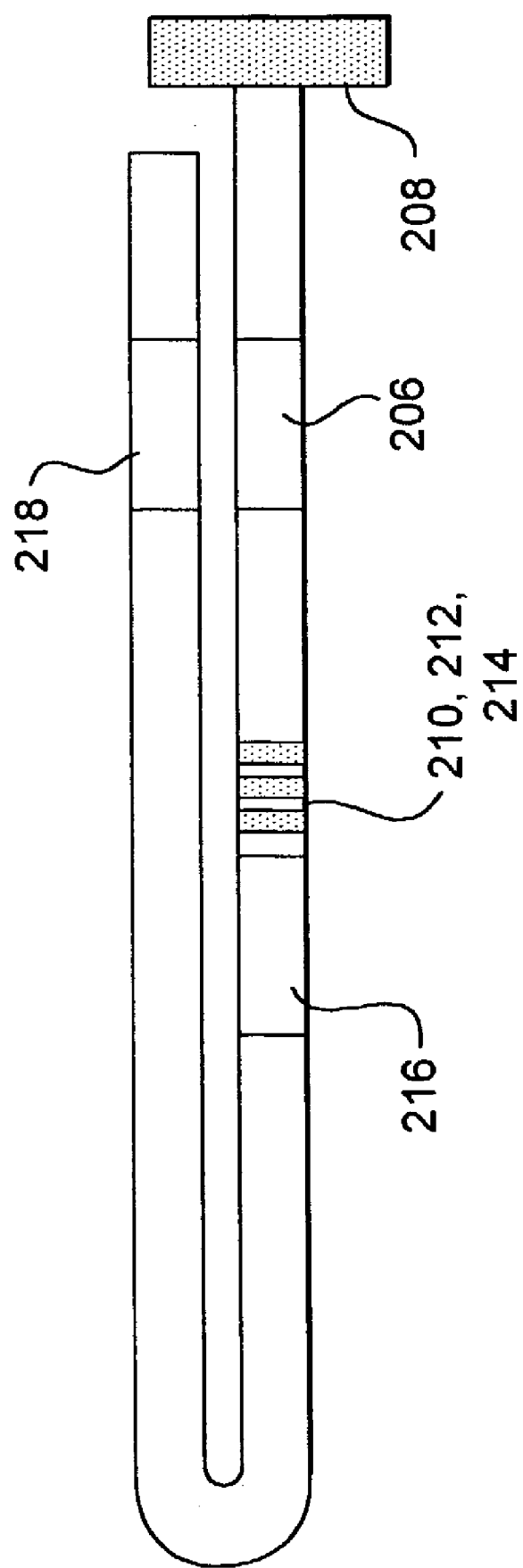
FIG. 4 illustrates a test strip design where the sample addition zone is positioned adjacent the wash buffer addition zone.

It is noted that the layout of the test strip illustrated in FIG. 1 is linear in design. However, non-linear layouts, such as the layout illustrated in FIG. 4, are also intended for the test strips according to the present invention.

FIGS. 2A–2H illustrate a method of operation of a lateral flow test strip, such as the one illustrated in FIG. 1. Prior to performing an assay using a test strip according to the present invention, a fluid sample is obtained that is believed to contain the analyte to be detected. The sample can include any fluid that wets the test strip and has a viscosity that is sufficient to allow movement of the sample across the test strip. In a preferred embodiment, the sample is an aqueous solution (such as a bodily fluid).

Figure 2A:
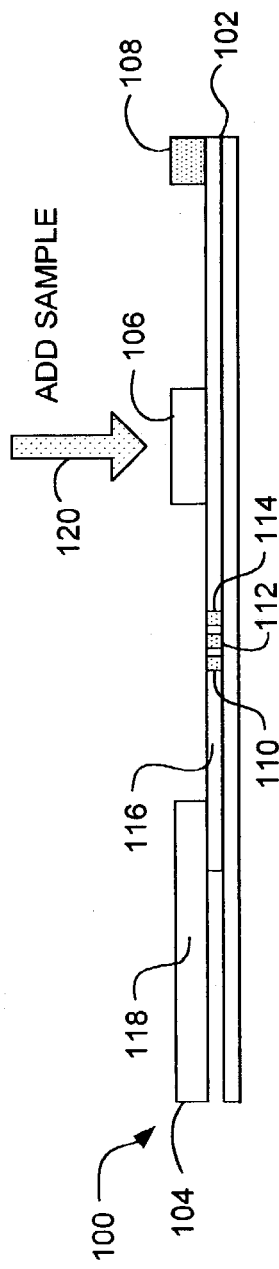
FIGS. 2A–2H illustrate a method of operation for a lateral flow test strip according to the present invention.

FIG. 2A illustrates the sample 120 being added to a sample addition zone 106 of the test strip 100. It is noted that the test strip is designed for use with a sample that has a volume within a particular range. More specifically, delivering a sample within the predetermined range causes the sample to diffuse distally beyond the test zones into the terminal sample flow zone 116, but not beyond the terminal sample flow zone 116 (as illustrated in FIG. 2D).

Figure 2B:
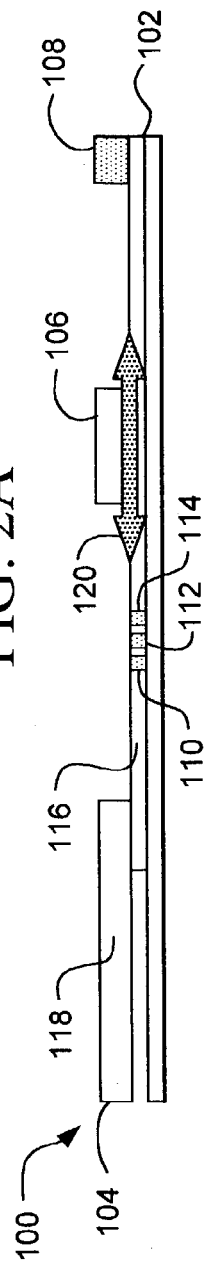
Figure 2C:
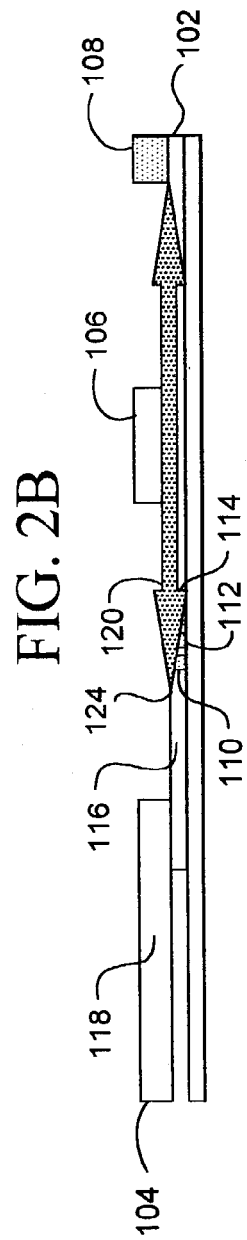
Figure 2D:
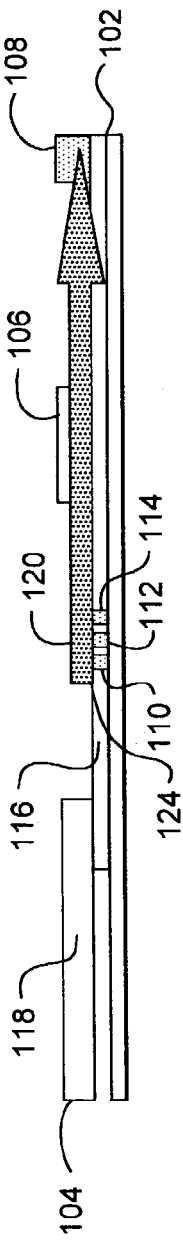

As illustrated in FIG. 2B, the sample 120 begins to diffuse both proximally and distally across the test strip after being added to the test strip. As illustrated in FIG. 2C, the distal front 124 of the sample 120 diffuses across the one or more test zones 110, 112, 114 to within the terminal sample flow zone 116. As illustrated in FIG. 2D, the distal front 124 of the sample 120 ultimately extends to a point within the terminal sample flow zone 116.

Figure 2E:
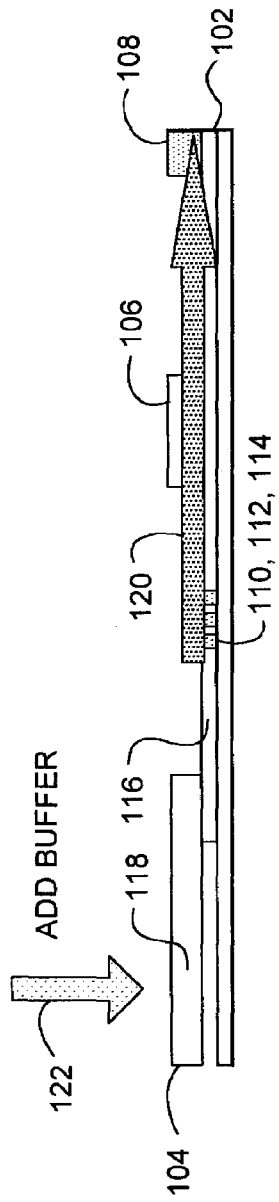

When the volume of the sample added to the test strip is within a predetermined volume range for which the test strip is designed, the distal front 124 of the sample 120 reaches a distal diffusion point corresponding to a point of maximum distal flow somewhere within the terminal sample flow zone 116. At this point, as illustrated in FIG. 2E, capillary action by the absorbent zone 108 draws the sample proximally toward the absorbent zone 108. As the sample is drawn into the absorbent zone 108, the distal front 124 of the sample recedes proximally.

As can be seen from FIGS. 2A–2D, a feature of the present invention is the control of where and how the sample flows within the test strip. The sample delivered to the test strip is preferably within a predetermined volume range that the test strip has been designed to process. The predetermined volume range is preferably between about 10 and 250 µL, preferably between about 20 and 100 µL, more preferably between about 30 and 50 µL, and most preferably between about 35 and 45 µL. When a sample is delivered to a test strip within these ranges, the flow of the sample stops within the terminal sample flow zone.

The terminal sample flow zone may be designed to have a short length from a proximal end to a distal end. For example, when a sample is delivered to the test strip within a range of about 35 and 45 µL, the terminal sample flow zone may have a length from a proximal end to a distal end of between about 1 and 25 mm, more preferably 2 and 15 mm, and most preferably 3 and 10 mm.

Positioned within one of the test zones (e.g., test zone 110) is a first analyte binding agent which binds to an analyte in the sample which the test strip is designed to detect. Analyte present in the portion of the sample which flows across the test zones is immobilized in test zone 110 by the first analyte binding agent.

FIG. 2E illustrates the addition of a conjugate buffer 122 to the test strip at conjugate buffer addition zone 118 after the sample has reached the terminal sample flow zone. The conjugate buffer 122 may contain one or more different second analyte binding agents which can bind to the analyte and enable analyte immobilized in the test zones to be detected. It is noted that the conjugate buffer addition zone 118 may optionally include the one or more second analyte binding agents used to detect immobilized analyte. In that instance, addition of the conjugate buffer 122 serves to initiate diffusion of the one or more second analyte binding agents across the test zones.

Figure 2F:
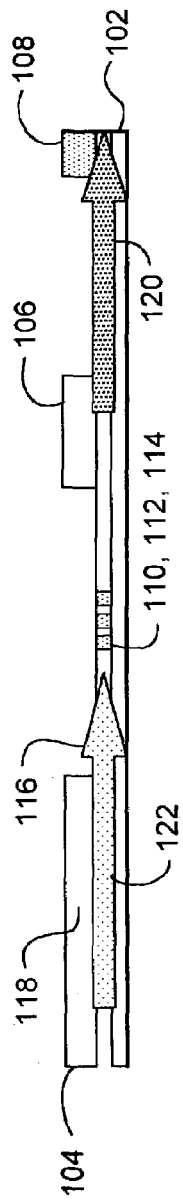
Figure 2G:
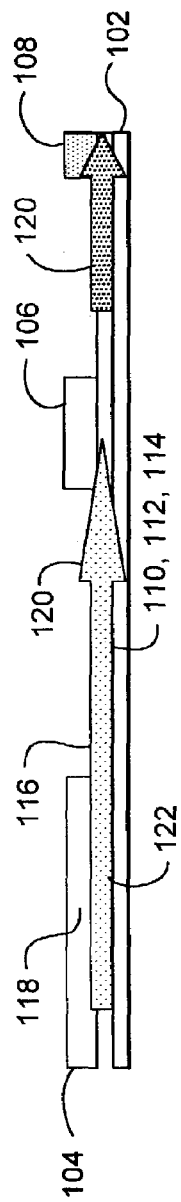

As illustrated in FIGS. 2F and 2G, the conjugate buffer 122 flows proximally across the test strip toward the absorbent zone 108, thereby causing the one or more second analyte binding agents to move across the test zones 110, 112, 114 and bind to immobilized analyte.

Figure 2H:
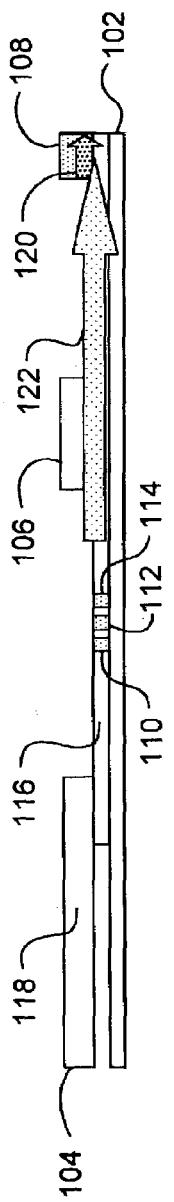

As illustrated in FIG. 2H, capillary action by the absorbent zone 108 causes the sample 120 to diffuse into the absorbent zone 108. Meanwhile, the conjugate buffer 122 continues to diffuse proximally across the test zones 110, 112, 114 and into the absorbent zone 108. Any of the one or more second analyte binding agents that were not immobilized in the test zones 110, 112, 114 are carried with the conjugate buffer 122 into the absorbent zone 108.

In regard to the embodiment illustrated in FIGS. 2A–2H, it is noted that the conjugate buffer 122 should be added to the test strip after the sample 120 has reached the test zones 110, 112, 114 and preferably after the sample has reached the terminal sample flow zone 116 and has begun to diffuse back toward the absorbent zone 108. This allows the portion of the sample 120 which flows across the test zones to contact the first analyte binding agents in the test zones with no conjugate buffer present.

FIGS. 3A–3H illustrate an alternative test strip design and method of operation for the test strip. In this embodiment, the sample and conjugate buffer are added at the same time. In order for the sample and conjugate buffer to be added at about the same time, it is necessary for the conjugate buffer to reach the test zones 210, 212, 214 after the sample has contacted the test zones. It is preferred that the conjugate buffer reach the test zones after the sample has begun diffusing back across the test zones toward the absorbent zone 208.

Delaying when the conjugate buffer reaches the test zones is accomplished in this embodiment by creating a longer distance between conjugate buffer addition zone 218 and the terminal sample flow zone 216 as compared to the test strip design illustrated in FIGS. 2A–2H. Alternatively, one can use a material which causes the conjugate buffer to diffuse at a slower rate.

Figure 3A:
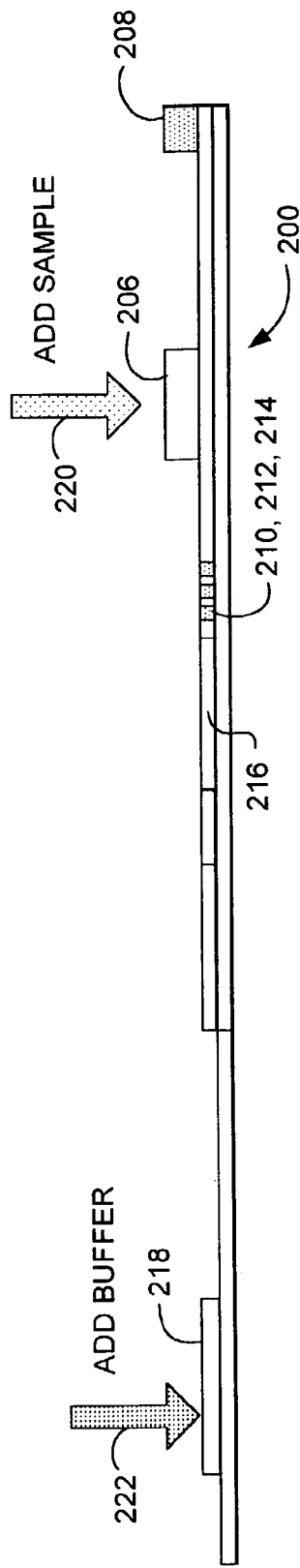
FIGS. 3A–3H a method of operation for a lateral flow test strip according to the present invention.

FIG. 3A illustrates a sample 220 being added to a sample addition zone 206 of the test strip 200. Meanwhile, a conjugate buffer 222 is added to a conjugate buffer addition zone 218 at about the same time that the sample is added to the test strip.

Figure 3B:
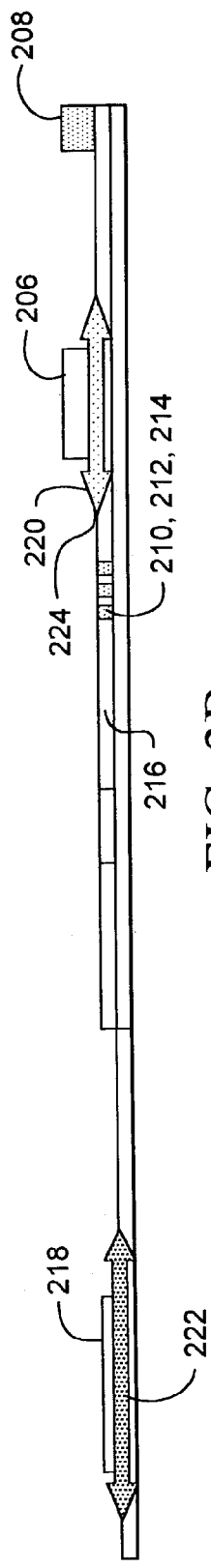

As illustrated in FIG. 3B, the sample 220 begins to diffuse both proximally and distally within the test strip once added to the test strip. Meanwhile, the conjugate buffer 222 also diffuses proximally and distally within the test strip.

Figure 3C:
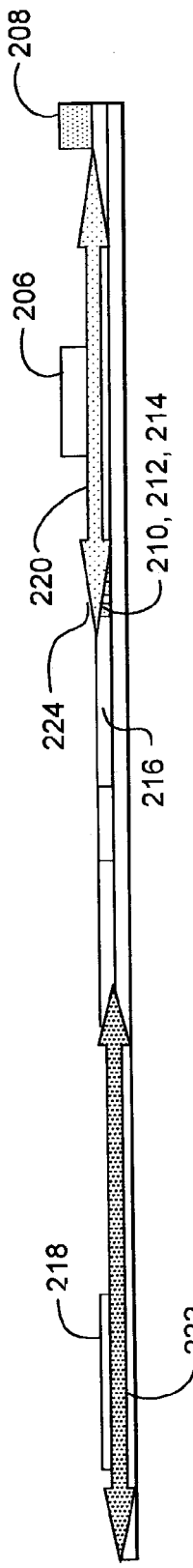

As illustrated in FIG. 3C, the distal front 224 of the sample 220 diffuses across one or more test zones 210, 212, 214 to within a terminal sample flow zone 216. Meanwhile, the conjugate buffer 222 continues to diffuse proximally within the test strip toward the test zones.

Figure 3D:
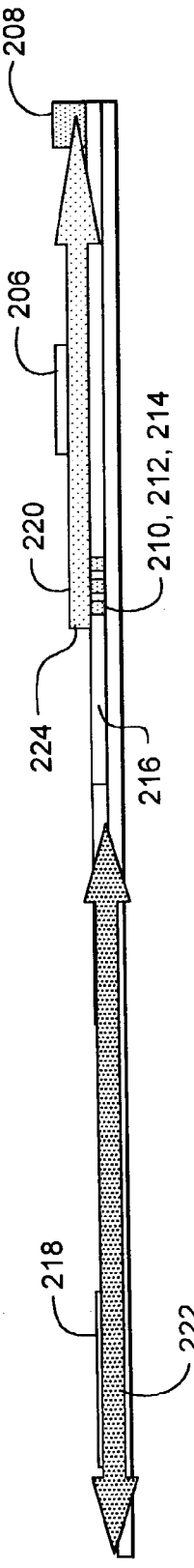

As illustrated in FIG. 3D, the distal front 224 of the sample 220 ultimately extends to a point within the terminal sample flow zone 216. At the time when the sample is in the terminal sample flow zone 216, the conjugate buffer 222 has not yet reached that zone.

Figure 3E:
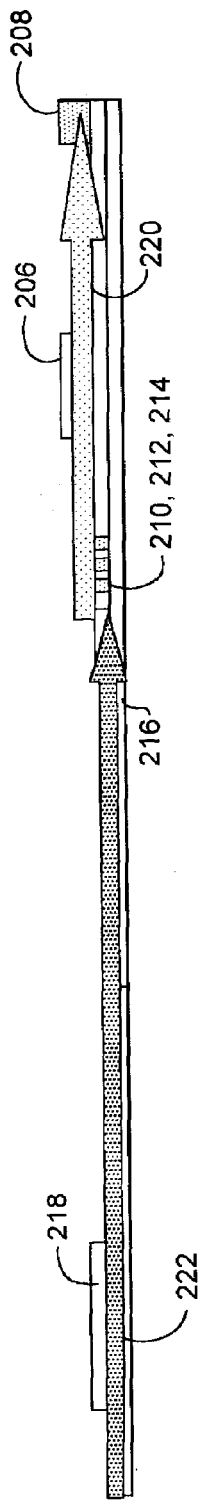

As illustrated in FIG. 3E, capillary action by the absorbent zone 208 draws the sample proximally toward the absorbent zone 208. As the sample is drawn into the absorbent zone 208, the distal front 224 of the sample flows proximally. Positioned within one of the test zones (e.g., test zone 210) is a first analyte binding agent which binds to analyte in the sample which the test strip is designed to detect. Analyte present in the portion of the sample which flows across the test zones is immobilized in test zone 210 by the first analyte binding agent.

Figure 3F:
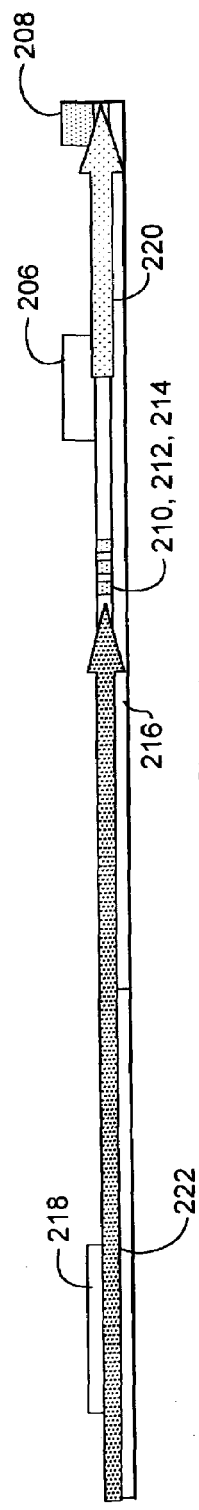

FIG. 3F illustrates the conjugate buffer 222 reaching the test zones. As can be seen, by the time the buffer 222 reaches the test zones, the distal front 224 of the sample has already flowed proximally out of the terminal sample flow zone 216 and the test zones 210, 212, 214.

Figure 3G:
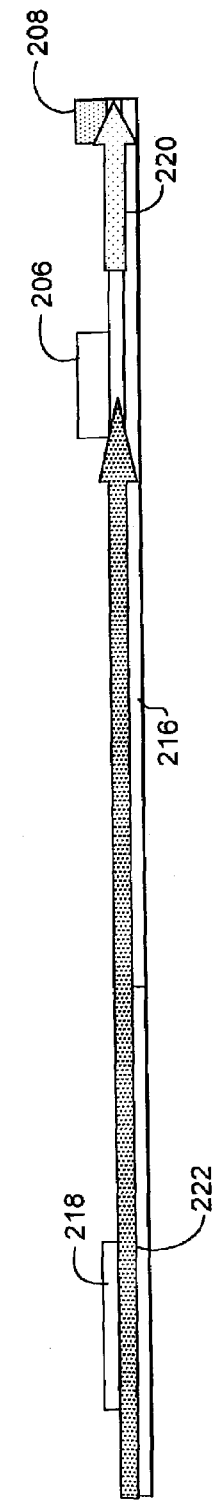
Figure 3H:
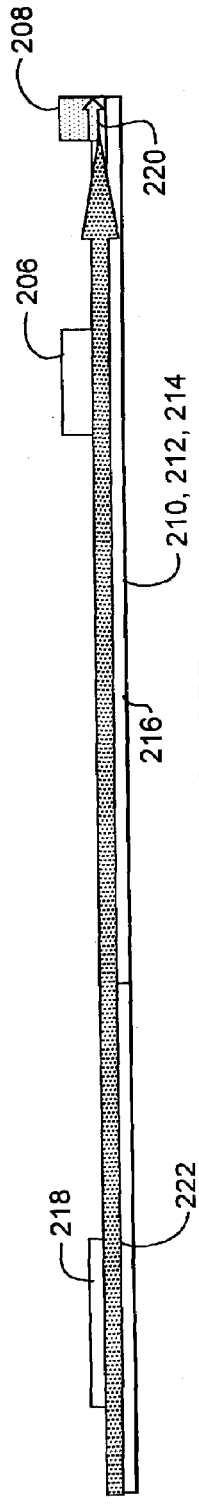

As illustrated in FIGS. 3G and 3H, capillary action by the absorbent zone 208 causes the sample to withdraw into the absorbent zone 208. Meanwhile, the buffer 222 continues to diffuse proximally across the test zones 210, 212, 214 and into the absorbent zone 208. Any of the one or more second analyte binding agents that were not immobilized in the test zones 210, 212, 214 are carried with the conjugate buffer 222 into the absorbent zone 208.

The conjugate buffer 222 added to the test strip may contain one or more second analyte binding agents which can bind to the analyte and enable analyte immobilized in the test zones to be detected. Alternatively, the test strip may include a conjugate zone distal to the terminal sample flow zone 216 which contains one or more second analyte binding agents. The conjugate buffer addition zone 218 may also serve as the conjugate zone. When the one or more second analyte binding agents are preloaded onto the test strip, the conjugate buffer 222 serves to initiate diffusion of the one or more second analyte binding agents across the test zones toward the absorbent zone.

As illustrated in FIGS. 3A–3H, the conjugate buffer may be added to the test strip before the sample reaches the test zones by designing the diffusion path of the test strip such that the conjugate buffer does not reach the test zones until after the sample has diffused from the test zones. It is noted that the diffusion of the conjugate buffer to the test zones may be sufficiently delayed that one adds the conjugate buffer to the test strip prior to adding the sample to the test strip.

FIG. 4 illustrates an alternative test strip design for a lateral flow test strip according to the present invention. The operation of the test strip is similar to the operation described in FIGS. 3A–3H. The same reference numerals are employed in FIG. 4 as in FIGS. 3A–3H. As illustrated in FIG. 4, the sample addition zone 206 is positioned adjacent the conjugate buffer addition zone 218. This allows for a more compact test strip design while also allowing the sample and conjugate buffer to be added simultaneously.

One feature of the test strip design illustrated in FIG. 4 is that the sample and conjugate buffer are added to the same end of the test strip. It is also noted that the test zones 210, 212, 214 are positioned toward an opposite end of the sample and conjugate buffer addition zones 206, 218. This makes it possible for the test zones to be positioned within a sample reader while the sample and conjugate buffer addition zones are outside the sample reader. This, in turn, allows sample and conjugate buffer to be added to the test strip while the test strip is in a test strip reader.

Figure 5A:
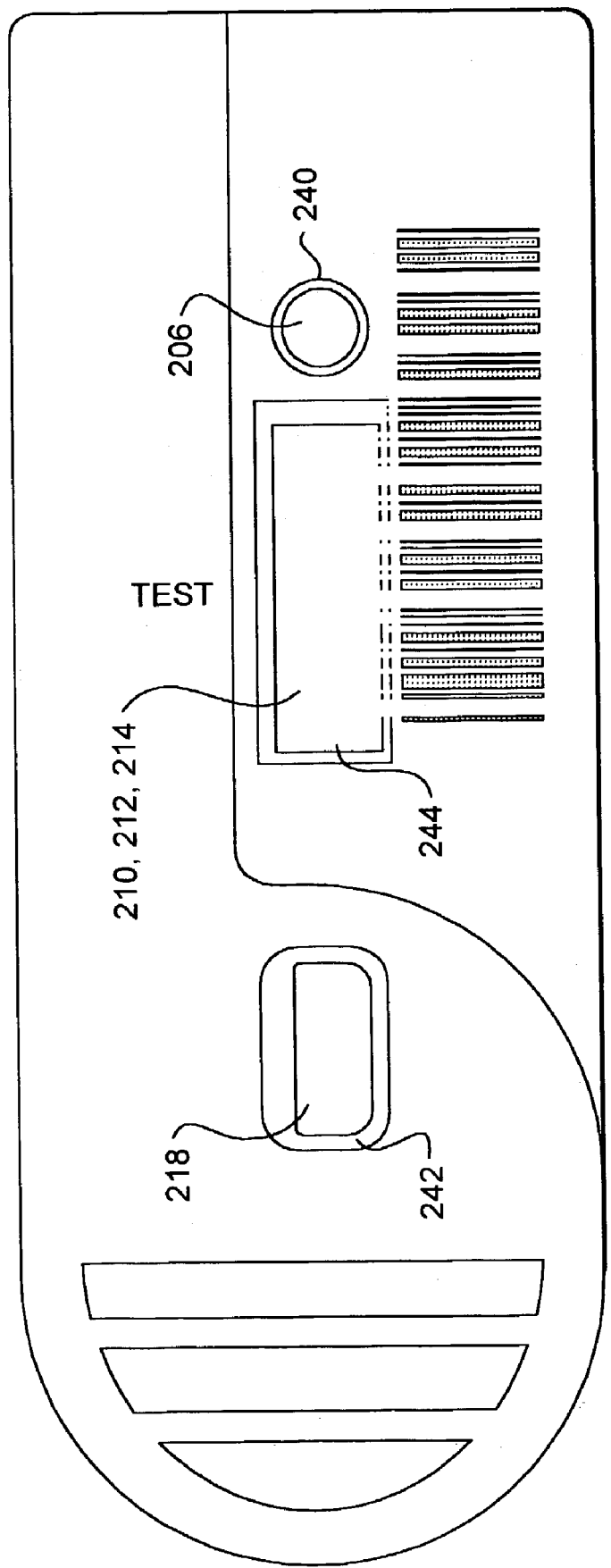
FIGS. 5A–5C illustrate various cartridge designs into which a test strip according to the present invention can be positioned.
Figure 5B:
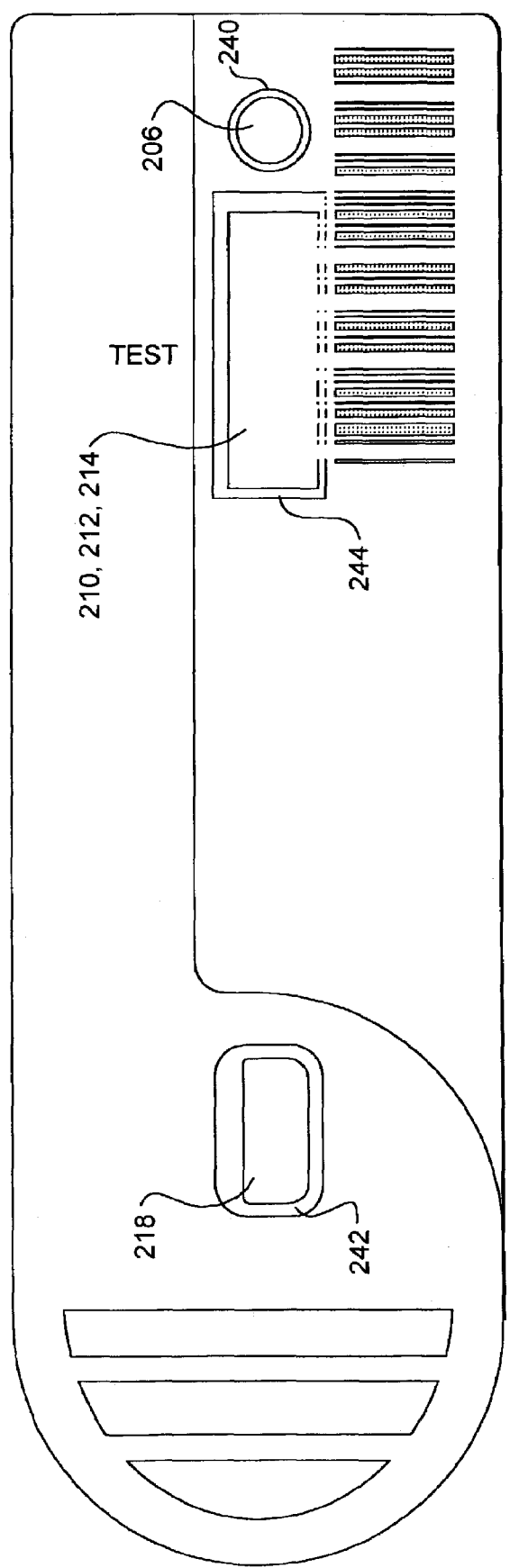
Figure 5C:
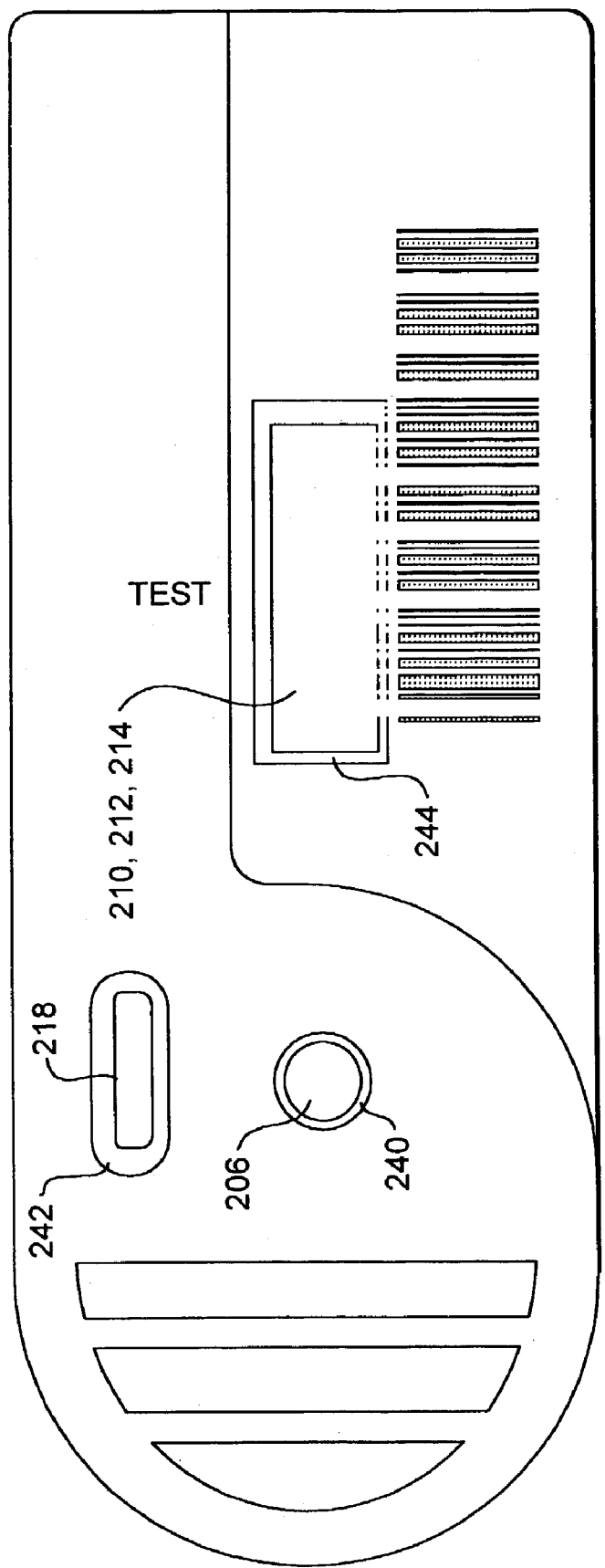

FIGS. 5A–5C illustrate various cartridge designs into which test strips according to the present invention can be positioned. In each cartridge design, the cartridge includes a sample addition port 240 adjacent the sample addition zone 206 of the test strip. The cartridge also includes a conjugate buffer addition port 242 adjacent the conjugate buffer addition zone 218 of the test strip. The cartridge also includes a test window 244 adjacent the test zones 210, 212, 214 of the test strip.

FIG. 5A illustrates a cartridge design adapted for the test strip illustrated in FIGS. 2A–2H. FIG. 5B illustrates a cartridge design adapted for the test strip illustrated in FIGS. 3A–3H where the sample addition zone is positioned an extended distance from the conjugate buffer addition zone such that the sample and conjugate buffer can be added to the test strip at about the same time. FIG. 5C illustrates a cartridge design adapted for the test strip illustrated in FIG. 4 where the sample addition zone is positioned adjacent the buffer addition zone, the test zone being positioned an extended distance from the buffer addition zone.

It is noted with regard to FIGS. 2–4 that a feature of the test strips of the present invention is the test strip's inherent ability to expose test zones on the test strip to a portion of the sample for a period of time and then to cause the sample to diffuse away from the test zones prior to conjugate buffer reaching the test zones. This feature is made possible by matching (1) the positioning of the absorbent zone relative to the sample addition zone with (2) the absorbent capacity of the test strip between the sample addition zone and the terminal sample flow zone and (3) the volume of the sample to be delivered to the test strip. If too much sample is delivered, the sample will diffuse beyond the terminal sample flow zone. If too little sample is delivered, the sample does not diffuse far enough in the test strip to reach the test zones.

The test strip's ability to expose the test zones to sample for a limited period of time and then cause the sample to be removed from the test zones confers a timing independence to the test strip which enhances the test strip's precision and ease of use. For example, as detailed in Example 2, test results are not dependent on when conjugate buffer is added to the sample. As a result, the test strips need not be carefully monitored regarding when conjugate buffer should be added. In this regard, the window of time after the sample has been added when conjugate buffer should be added to the test strip is eliminated by the present invention.

The dynamics of using the volume of the sample delivered to the test strip to control how the sample diffuses within the test strip will now be illustrated in regard to FIG. 1. As discussed previously, FIG. 1 illustrates a test strip which has proximal and distal ends 102, 104 respectively and is divided into several distinct zones. The test strip includes a sample addition zone 106 where a sample is added to the test strip. An absorbent zone 108 is positioned proximal to the sample addition zone 106. A test zone 110 is positioned distal to the sample addition zone 106. A terminal sample flow zone 116 is positioned distal to the test zone 110. A conjugate buffer addition zone 118 is positioned distal to the terminal sample flow zone 116.

For the purpose of illustration, assume that the test zone 110 includes a first analyte binding agent and the conjugate buffer addition zone 118 includes a second analyte binding agent labeled with a detectable marker. Also assume that the test strip is designed such that a sample volume of 30 μL will cause the sample to diffuse to but not beyond the test zone 110. Meanwhile, a sample volume of 50 μL will cause the sample to diffuse to the distal end of the terminal sample flow zone 116.

If a sample is delivered to the test strip within the 30–50 μL volume range, the distal front of the sample will diffuse past the test zone 110. Distal advancement of the sample will stop within the terminal sample flow zone 116. Analyte in the portion of the sample which reaches the test zone 110 will bind to the first antibody and become immobilized in the test zone 110. Other components in the sample will not bind to the first antibody since the first antibody is selective for the analyte. The sample then flows back in the proximal direction toward the absorbent zone 108 past the test zone 110. When the conjugate buffer is added, the conjugate buffer causes the second analyte binding agent to diffuse across the test zone 110 where the second analyte binding agent binds to the analyte immobilized in the test zone 110. Since the sample diffuses away from the test zone 110 prior to the buffer reaching the test zone 110, no agents from the sample are present that might otherwise bind to the second analyte binding agent. As a result, the analyte to be detected in the sample does not have to compete with other agents in the sample in order to bind to the second analyte binding agent.

If a sample volume of less than 30 μL is delivered (e.g., 25 μL) to the test strip, the sample never diffuses to the test zone 110. As a result, none of the analyte in the sample reaches the test zone 110 and binds to the first antibody. When the buffer is added, the second analyte binding agent is carried with the diffusion of the conjugate buffer and traverses the test zone 110 without becoming immobilized since no analyte is present in the test zone.

If the sample volume delivered is greater than 50 μL (e.g., 55 μL), the sample will diffuse past the test zone 110 and past the terminal sample flow zone 116 into the conjugate buffer addition zone. Some of the analyte will bind to the first analyte binding agent in test zone 110 and become immobilized. Meanwhile, some analyte will bind to the second analyte binding agent in the conjugate buffer addition zone 118 prior to flowing back and binding to the first analyte binding agent in the test zone 110. Analyte which binds to two copies of the second analyte binding agent are unlikely to bind to the first analyte binding agent due to steric hindrance. Also, it may be more difficult to bind the analyte to the first analyte binding agent after the analyte has already bound to the second analyte binding agent. As a result, the sensitivity of the test strip may be reduced if the analyte binds to the second analyte binding agent before binding to the first analyte binding agent. Other components in the portion of the sample which reaches the conjugate buffer addition zone 118 may also bind to the second analyte binding agent. These other components will compete with the analyte for binding to the second analyte binding agent.

By controlling the volume of the sample delivered and thereby (1) exposing the analyte to the first analyte binding agent prior to exposing the immobilized analyte to the second analyte binding agent, and (2) not exposing the second analyte binding agents to the analyte prior to being exposed to other components in the sample, non-specific binding is reduced which significantly improves assay sensitivity and analyte detection precision.

As has been described above, two advantages of the test strips of the present invention are their self-washing and self-timing properties. In order to explain the significance of these properties, a comparison will now be made to the FLEXPACK™HP test strip manufactured by Abbott which is illustrated in FIGS. 6A and 6B.

Figure 6A:
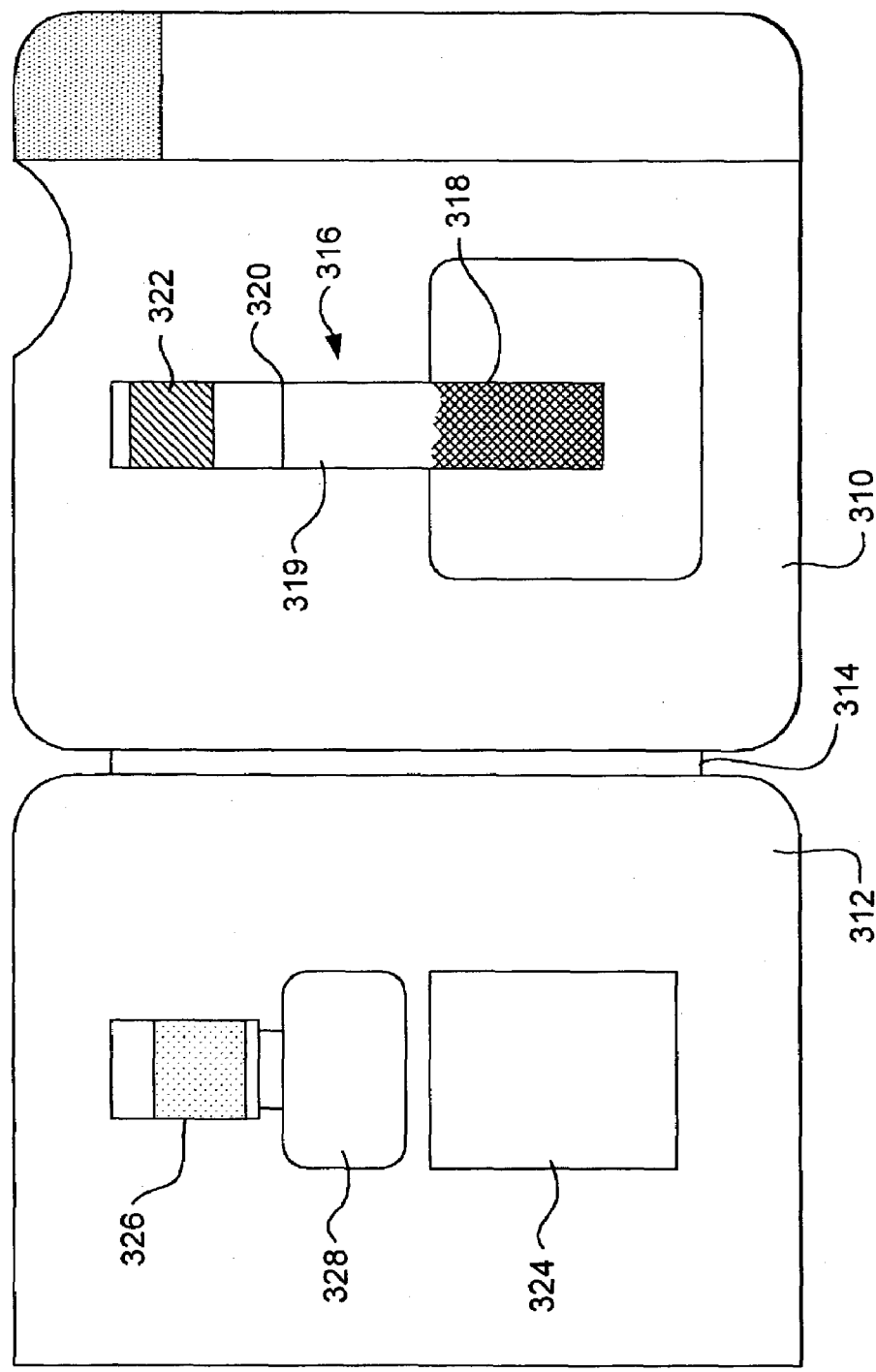
FIG. 6A illustrates the layout of a FLEXPACK™HP test strip manufactured by Abbott.

FIG. 6A illustrates the layout of the test strip. As illustrated, the test strip includes two separate sections 310, 312 which are attached to each other by a hinge 314. Section 310 on the right includes a test strip 316 which includes a sample addition zone 318, a test zone 319, a limit line 320, and a conjugate buffer transfer pad 322. Section 312 on the left includes an absorbent pad 324 which is positioned opposite the sample addition zone 318, a conjugate buffer addition pad 326 which is positioned opposite the conjugate buffer transfer pad 322, and a test window 328 which is positioned opposite the test zone 319. The apposing positionings of the absorbent pad 324, the conjugate buffer addition pad 326, and the test window 328 allows the absorbent pad 324 to contact the sample addition zone 318 and the conjugate buffer addition pad 326 to contact the conjugate buffer transfer pad 322 when the first and second sections 310, 312 are brought into contact with each other. In addition, the test zone 319 can be seen through the test window 328 when the first and second sections 310, 312 are brought together.

Figure 6B:
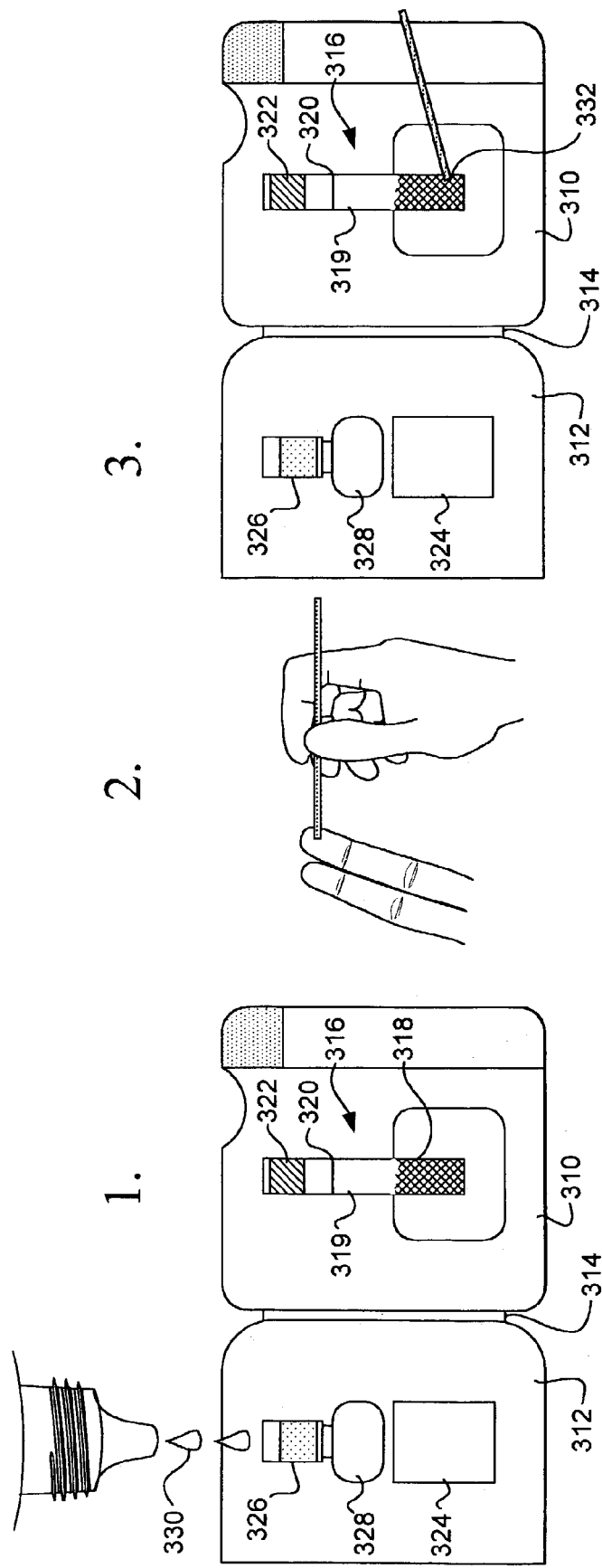
FIG. 6B illustrates the operation of the test strip illustrated in FIG. 6A.

FIG. 6B illustrates the operation of the test strip illustrated in FIG. 6A. As illustrated, a conjugate buffer 330 is added to the conjugate buffer addition pad 326. The conjugate buffer addition pad 326 includes a second analyte binding agent (e.g., an antibody) capable of binding to an analyte in the sample to be detected. The second analyte binding agent is labeled with a detectable marker which allows the second analyte binding agent to be visualized. The second analyte binding agent is not specific for the analyte and thus can bind to other components in the sample.

A sample 332 is then taken and added to the sample addition zone 318. Once added, the sample diffuses through the test strip 316 from the sample addition zone 318 across the test zone 319. The test zone 319 includes an immobilized first analyte binding agent (e.g., an antibody) which selectively binds to an analyte in the sample which the test strip is designed to detect. When the sample traverses the test zone 319, analyte in the sample binds to the first analyte binding agent and is immobilized in the test zone 319.

When the diffusion front of the sample reaches the limit line 320, the user is supposed to bring the first and second sections 310, 312 together. Bringing the first and second sections 310, 312 together causes the absorbent pad 326 to draw the sample back toward the sample addition zone 318. Meanwhile, conjugate buffer is transferred to the conjugate buffer transfer pad 322 from the conjugate buffer addition pad 320. The conjugate buffer diffuses from the conjugate buffer transfer pad 322 across the test zone 319. Second analyte binding agent that was stored in the conjugate buffer addition zone 318 diffuses with the conjugate buffer and contacts immobilized analyte in the test zone 319. Observation of the visually detectable marker on the second analyte, binding agent once immobilized in the test zone 319, is used to detect the analyte.

As can be seen from the above description of the operation of the FLEXPACK™HP test strip, it is necessary to determine when the sample reaches the limit line 320 before causing the conjugate buffer to be transfered from the buffer addition pad 318 to the conjugate buffer addition pad 320 and begin flowing toward the test zone 319. It is also necessary to take the affirmative step of contacting the sample addition zone 318 with the absorbent pad 324 in order to cause the sample to be withdrawn from the test zone 319. The design of the test strips of the present invention, for example those illustrated in FIGS. 2–4, eliminate the need to monitor the test strip to determine when to begin the removal of the sample from the test zone. In addition, since the sample withdraws automatically, one need not carefully monitor the test strip regarding when to add the conjugate buffer. Rather, as shown in Example 2, test results using the test strips of the present invention are not dependent on when the conjugate buffer reaches the test zones after the sample diffuses from the test zones.

Lateral flow assays according to the invention may find use in a variety of applications. For example, the assays may be used to assay for human diseases, such as infectious diseases, or any other human diseases involving recognizable epitopes (e.g. cancer, autoimmune disease, cardiovascular conditions and pathology). The assays may also be used in veterinary, food testing, agricultural, or fine chemical applications. The lateral flow assays according to the invention may be performed in variety of ways, including use of a lateral flow assay testing apparatus, such as that disclosed in the application Ser. No. 09/199,255, filed Nov. 23, 1998 which is incorporated herein by reference. In a preferable embodiment, the lateral flow assay testing apparatus comprises a ReLIA™ testing apparatus, available from PraxSys BioSystems (San Ramon, Calif.).

1. Construction of Test Strips According to the Present Invention

Methods and materials for constructing test strips according to the present invention will now be discussed in greater detail. It is noted that the particular construction of the test strip may be varied, depending on the particular assay that the test strip is intended to perform. Variations in the way in which the test strips may be constructed beyond this example are intended to fall within the scope of the invention.

Figure 7:
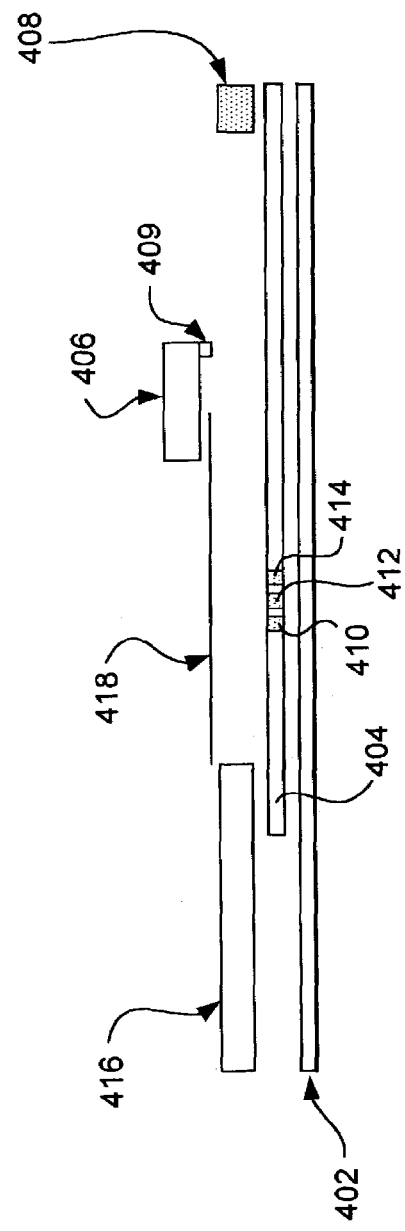
FIG. 7 illustrates a side break-away view of the lateral flow test strip illustrated in FIG. 1.

FIG. 7 illustrates a side break-away view of the lateral flow test strip illustrated in FIG. 1. As illustrated in FIG. 7, the test strip 100 may include a backing strip 402 which runs a length of the test strip. A membrane strip 404 is positioned over the backing strip 402 and serves as a diffusion passageway for the test strip. An absorbent pad 408 is positioned over the membrane strip 404 within the absorbent zone 108 which is positioned toward a proximal end of the test strip. A sample pad 406 is positioned over the membrane strip 404 distal to the absorbent pad 408. An adhesive 409 may be used to attach the sample pad 406 to the membrane strip 404. One or more test zones 410, 412, 414 may be formed in the membrane strip 404 distal to the sample pad 406. A conjugate buffer addition pad 416 is positioned over the membrane strip 404 distal to the test zones 410, 412, 414 and distal to the terminal sample flow zone 116. A protective cover 418 is positioned over the test zones. To allow air bubbles trapped between fluid fronts to escape, a gap is left between the test and conjugate zones that is not covered by the protective cover 418. The protective cover 418 may also be positioned more broadly over the membrane strip 404 in order to protect other portions of the test strip.

The backing strip may be made of any stable, non-porous material that is sufficiently strong to support the materials and strips coupled to it. Since many assays employ water as a diffusion medium, the backing strip is preferably substantially impervious to water. In a preferred embodiment, the backing strip is made of a polymer film, more preferably a poly(vinyl chloride) film.

The membrane strip may be made of any substance which has sufficient porosity to allow capillary action of fluid along its surface and through its interior. The membrane strip should have sufficient porosity to allow movement of antibody- or antigen-coated particles. The membrane strip should also be wettable by the fluid used in the sample which contains the analyte to be detected (e.g., hydrophilicity for aqueous fluids, hydrophobicity for organic solvents). Hydrophobicity of a membrane can be altered to render the membrane hydrophilic for use with aqueous fluid, by processes such as those described in U.S. Pat. No. 4,340,482, or U.S. Pat. No. 4,618,533, which describe transformation of a hydrophobic surface into a hydrophilic surface. Examples of substances which can be used to form a membrane strip include: cellulose, nitrocellulose, cellulose acetate, glass fiber, nylon, polyelectrolyte ion exchange membrane, acrylic copolymer/nylon, and polyethersulfone. In a preferred embodiment, the membrane strip is made of nitrocellulose.

The absorbent pad may be formed of an absorbent substance that can absorb the fluid used as the sample and buffer. The absorption capacity of the absorbent pad should be sufficiently large to absorb the fluids that are delivered to the test strip. Examples of substances suitable for use in an absorbent pad include cellulose and glass fiber.

The buffer addition pad may be formed of any absorbent substance. Examples of substances that may be used include cellulose, cellulose nitrate, cellulose acetate, glass fiber, nylon, polyelectrolyte ion exchange membrane, acrylic copolymer/nylon, and polyethersulfone.

As discussed previously, the conjugate buffer addition pad may serve as a conjugate pad and contain an agent labeled with a detectable marker which is capable of binding to the analyte to be detected in the sample. Alternatively, the test strip may include a conjugate pad separate from the buffer addition pad which contains an agent labeled with a detectable marker which is capable of binding to the analyte to be detected in the sample.

The protective cover may be formed of any material which is impervious to water, and is preferably translucent or transparent. The protective covering may be a single or multiple layers. Preferable materials for use in the protective covering include optically transmissive materials such as polyamide, polyester, polyethylene, acrylic, glass, or similar materials. The protective covering may be clear or not clear depending on method of detection used. In a preferable embodiment, protective covering is optically clear polyester.

2. Assays for Use with Test Strips According to the Present Invention

The test strips of the present invention are intended to be employable with a wide variety of lateral flow assays involving two analyte binding agents which each can bind to an analyte to be detected. At least one of the binding agents should bind selectively to the analyte. More specifically, one of the binding agents should bind to the analyte and not bind to any other components of the sample.

As used herein, the term, "analyte," is intended to refer to any component of a sample (e.g., molecule, compound, or aggregate thereof which is to be detected and optionally quantitatively determined by an assay test strip. Examples of analytes include proteins, such as hormones and other secreted proteins, enzymes, and cell surface proteins; glycoproteins; peptides; small molecules; polysaccharides; antibodies (including monoclonal or polyclonal Ab and portions thereof; nucleic acids; drugs; toxins; viruses or virus particles; portions of a cell wall; and other compounds possessing epitopes.

The first and second analyte binding agents may be any agents which can bind to the analyte to be detected. A variety of different types of molecules can be used as analyte binding agents, including, for example, antibodies, engineered proteins, peptides, haptens, and lysates containing heterogeneous mixtures of antigens having analyte binding sites. P. Holliger et al., Trends in Biotechnology 13:7–9 (1995); S. M. Chamow et al., Trends in Biotechnology 14:52–60 (1996). If the analyte to be detected is a ligand, a receptor which binds to the ligand can be used, and vice versa. In one particular embodiment, the first and/or second analyte binding agents are antibodies which bind to an immunogenic portion of the analyte.

It is noted that at least one of the first and second analyte binding agents should bind to the analyte and not bind to any of the other components in the sample to be analyzed, referred to herein as an analyte-selective binding agent. In one embodiment, the first analyte binding agent which is immobilized in a test zone is an analyte-selective binding agent and the second analyte binding agent which is labeled with a detectable marker is capable of binding non-selectively to the analyte. In another embodiment, the first analyte binding agent which is immobilized in a test zone is capable of binding non-selectively to the analyte and the second analyte binding agent which is labeled with a detectable marker is an analyte-selective binding agent. In yet another embodiment, both the first and second analyte binding agents are analyte-selective binding agents.

Examples of analyte-selective binding agents include antibodies (monoclonal, polyclonal, and fragments thereof) which have a narrow binding affinity to only a particular type of biomolecule, such as a protein or receptor.

The detectable marker attached to the second analyte binding agent may comprise a wide variety of materials, so long as the marker can be detected. Examples of detectable markers include, but are not limited to particles, luminescent labels; colorimetric labels, fluorescent labels; chemical labels; enzymes; radioactive labels; or radio frequency labels; metal colloids; and chemiluminescent labels. Examples of common detection methodologies include, but are not limited to optical methods, such as measuring light scattering, simple reflectance, luminometer or photomultiplier tube; radioactivity (measured with a Geiger counter, etc.); electrical conductivity or dielectric (capacitance); electrochemical detection of released electroactive agents, such as indium, bismuth, gallium or tellurium ions, as described by Hayes et al. (Analytical Chem. 66:1860–1865 (1994)) or ferrocyanide as suggested by Roberts and Durst (Analytical Chem. 67:482–491 (1995)) wherein ferrocyanide encapsulated within a liposome is released by addition of a drop of detergent at the detection zone with subsequent electrochemical detection of the released ferrocyanide. Other conventional methods may also be used, as appropriate.

It may be desired to assay two or more different analytes using the same test strip. In such instances, it may be desirable to employ different detectable markers on the same test strip where each detectable marker detects a different analyte. For example, different detectable markers may be attached to different analyte-selective binding agents. The different detectable markers may be different fluorescent agents which fluoresce at different wavelengths.

When detecting two or more different analytes using the same test strip, separate test zones may optionally be formed on the test strip for each analyte to be detected. The same detectable marker may be used for all of the analytes. Alternatively, different detectable markers, as described above, may be used for the different analytes in order to prevent one test zone being confused with another.

In a preferable embodiment, the detectable marker is a particle. Examples of particles that may be used include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads.

A preferred class of particles is colloidal gold particles. Colloidal gold particles may be made by any conventional method, such as the methods outlined in G. Frens, 1973 Nature Physical Science, 241:20 (1973). Alternative methods may be described in U.S. Pat. Nos. 5,578,577, 5,141,850; 4,775,636; 4,853,335; 4,859,612; 5,079,172; 5,202,267; 5,514,602; 5,616,467; 5,681,775.

The selection of particle size may influence such factors as stability of bulk sol reagent and its conjugates, efficiency and completeness of release of particles from conjugate pad, speed and completeness of the reaction. Also, particle surface area may influence steric hindrance between bound moieties. Particle size may also be selected based on the porosity of the membrane strip. The particles are preferably sufficiently small to diffuse along the membrane by capillary action of the conjugate buffer.

Particles may be labeled to facilitate detection. Examples of labels include, but are not limited to, luminescent labels; colorimetric labels, such as dyes; fluorescent labels; or chemical labels, such as electroactive agents (e.g., ferrocyanide); enzymes; radioactive labels; or radio frequency labels.

The number of particles present in the test strip may vary, depending on the size and composition of the particles, the composition of the test strip and membrane strip, and the level of sensitivity of the assay. The number of particles typically ranges between about $1\times10^9$ and about $1\times10^{13}$ particles, although fewer than about $1\times10^9$ particles may be used. In a preferred embodiment, the number of particles is about $1\times10^{11}$ particles.

3. Control Test Zones

As illustrated in FIG. 1, a plurality of test zones 110, 112, 114 may be included on the test strip. Each test zone is located such that an automatic or semi-automatic analytical instrument, or a human reader, may determine certain results of the lateral flow assay.

As discussed previously, immobilized in at least one of the test zones is a first analyte binding agent which is capable of binding to an analyte in the sample which the test strip is designed to detect. In some embodiments, it may be desirable for some of the other test zones to include one or more control zones where one or more control binding agents have been immobilized. Control agents capable of binding to the control binding agent may be positioned on the test strip at various locations or added to the test strip when the assay is being performed. The control agents are preferably labeled with a detectable marker, such as the detectable markers described above, to facilitate detection of the control agent binding to the control binding agent immobilized in a control zone.

The control agents and control binding agents may be used in combination to perform a variety of control functions. For example, the control binding pairs may be used to confirm whether the sample and conjugate buffer have diffused properly within the test strip. The control binding pairs are also employable as internal standards and allow analyte measurement results to be compared between different test strips. This can be used to correct for strip-to-strip variability. Such correction would be impractical with external controls that are based, for example, on a statistical sampling of strips. Additionally, lot-to-lot and run-to-run variations between different test strips may be minimized by the use of control binding pairs. Furthermore, the effects of non-specific binding, as discussed further below, may be reduced. All of these corrections are difficult to accomplish using external, off-strip controls.

A wide variety of agents are known in the art which may be used as a member of the control binding pair. For example, at least one member of the control binding pair may be a naturally occurring or engineered protein. The control binding pair may also be a receptor—ligand pair. Additionally, at least one member of the control binding pair may be an antigen, another organic molecule, or a hapten conjugated to a protein non-specific for the analyte of interest. Descriptions of other suitable members of control binding pairs may be found in U.S. Pat. No. 5,096,837, and include IgG, other immunoglobulins, bovine serum albumin (BSA), other albumins, casein, and globulin.

Desirable characteristics for control agent—control binding agent pairs include, but are not limited to stability in bulk, non-specificity for analyte of interest, reproducibility and predictability of performance in test, molecular size, and avidity of binding for each other.

In a preferred embodiment, members of the control binding pair do not bind to anything that might be present in the test strip, e.g., from the sample. In one embodiment, the control binding agent comprises rabbit anti-dinitrophenol (anti-DNP) antibody and the control agent includes a dinitrophenol conjugated to BSA (bovine serum albumin).

In one preferred embodiment, both the second analyte binding agent which diffuses along the test strip and the control agent are attached to a single species of particle. Attachment may be by non-specific absorption or by traditional conjugate chemistries. Alternatively, a non-covalent binding system, such as biotin-avidin, or even an antibody specific for the second analyte binding agent may be used to attach the analyte binding agent to the particle. Bifunctional and multifunctional reagents may also be used to couple to the second analyte binding agent and the control agent to the particle.

The number of second analyte binding agents and control agents attached to each particle can be varied, depending on what is appropriate for a particular assay. For example, two copies of the second analyte binding, agent and one copy of the control agent may be attached to each particle. Alternatively, one copy of the second analyte binding agent and two copies of the control agent may be attached to each particle. Other variations on the ratios between second analyte binding agent:control agent:particle can be used depending on the particular assay in which they are to be employed, these variations being intended to fall within the scope of the present invention.

In a preferred embodiment, the test strip includes more than one control zone and is used to create a calibration curve against which a wide variety of analyte measurement results may be compared. This embodiment is described in greater detail in application Ser. No. 09/198,118, filed Nov. 23, 1998 which is incorporated herein by reference. Having the test strip possess more than one control zone allows lateral flow assays to have a wider dynamic range than conventional lateral flow assays. In preferred embodiments, test strips with 2, 3 or more control zones are used with a relative scale methodology, discussed further below, that permits mapping of amounts of control binding pairs detected onto the same scale on which amounts of analyte detected are reported.

In a preferred embodiment, the test strip has at least one high control zone and at least one low control zone. The difference between the two zones is generally one of concentration. The concentration of control agent in the high control zone is greater than the concentration of control agent in the low control zone. Thus, the amount of control binding pairs will be higher in the high control zone versus the low control zone. In embodiments where the amount of control binding pairs in a given control zone may be mapped onto the same measurement scale on which the amount of analyte is reported, a calibration curve may be drawn through the values of the binding pairs in the high and low control zones.

In other embodiments, more than two control zones may be present. This allows for a curve to be generated that better reflects any nonlinearities present in the assay between the amount of analyte detected and the measurement against which the amount might be mapped, as discussed below. While such nonlinearities might otherwise affect assays that assume a relatively linear relationship, they can be corrected for using multiple control zones. 2, 3 or more control zones may be used.

In another embodiment, a single control zone may comprise more than one type of control agent. This may be of use in embodiments where there are more than one population of analyte binding agents and analyte non-specific agents coupled to a detection agent. For example, when it is desired to assay two or more analytes of interest on the same assay strip, two populations of analyte binding agents and analyte non-specific agents coupled to a detection agent may be prepared. Different detection agents may be used for each population, allowing a distinction to be drawn between results for the two different analytes of interest. In such circumstances, it may be desirable to use control zones comprising different control agents or control binding pairs.

The control zones may be located in a variety of locations within the group of test zones. It is noted that the test zones may be placed on various locations on the test strip, depending on the flow design of the test strip consistent with the present invention.

Assays are performed using a test strip which includes one or more control regions as part of the test regions in the same manner as described in regard to FIGS. 2A–2H and 3A–3H. It is noted that either the test strip or conjugate buffer includes the control agent which binds to the control binding agent immobilized, for example, in test zones 112 and 114 of FIGS. 2A–2H and test zones 212 and 214 of FIGS. 3A–3H. When the conjugate buffer is added, the control agent diffuses with the conjugate buffer and binds to the control binding agent immobilized in the control zones.

Amounts of control agents immobilized in the control zones are detected along with the detection of amounts of second analyte binding agent immobilized in the test zones. As noted above, it is preferred for the control agents and the second analyte binding agent to be labeled with a detectable marker which facilitates their detection. The amount of detectable marker in each test zone can be readily determined by a variety of techniques known in the art, depending on the type of detectable markers being employed. Common examples of detection techniques include optical methods (light scattering, simple reflectance, luminometer or photomultiplier tube); radioactivity; electrical conductivity; dielectric capacitance; electrochemical detection of released electroactive agents; as has been noted above.

Once the amount of detectable markers has been measured in each test zone, these measurements may be used to detect and preferably quantify the amount of analyte present, preferably by also calibrating the test strip using the amounts of detectable markers in the control zones. For example, when high and low control zones are employed, the amount of control agent immobilized in the high and low control zones may be used to quantify the amount of second analyte binding agent relative to the high and low control zones. These relative intensity measurements may then be used to more accurately determine the number of copies of analyte present in the measurement volume.

One feature of using multiple control zones is the ability to create a relative scale for analyte measurements. Once the amounts of detectable markers have been quantified, these amounts may then be mapped onto another measurement scale. For example, while the results from measuring the analyte may be measured based on an absolute measurement of the analyte, the results reported may be more meaningful in other units, such as an intensity relative to that of a control zone or control zones, referred to herein as Relative Intensity or RI. Results may also be expressed as the number of copies of analyte present in the measurement volume. The mapping of the amount of analyte detected onto other measurement scales is a preferable embodiment for reporting results of the inventive assay.

For instance, the assay results may be mapped onto a relative scale. Using a relative scale, such as Relative Intensity (RI), for internal control(s), absolute values for the analyte detected may be converted into RI values. In a preferable embodiment, a low control may be assigned an RI value of 1 and a high control may be assigned an RI value of 3, even though the ratio of the absolute values of these controls may be different. In a preferable embodiment, the absolute value ratio may be at least about 5:1, while the RI ratio may be about 3:1. By so doing, changes in individual test strips affecting the absolute value measured will cause the standard curve to shift up and down a Y-axis, but will have a smaller impact on the RI value plotted along the X-axis. This will systematically damp the variability in the reported result, i.e. will manifest as a "negative gain."

For example, if there is a negative gain between the measured amount of analyte and the reported amount of analyte, then large changes in the measured amount of analyte will be mapped into relatively small changes in the reported amount of analyte. Although the underlying variability of the measured amount of analyte does not change, this method may be of use in certain circumstances. The negative gain effect damps some of the test variability and can be used to improve reproducibility of the reported results of the test as compared to simply reporting an absolute valve of what is measured.

In addition to reporting the assay results on a continuous scale, either directly as the amount of analyte detected or indirectly as a measurement scale onto which the amount of analyte detected has been mapped, the inventive assays may be used in a "cut-off" style assay. If the detectable marker is detected in an analyte binding zone, the amount of detectable marker detected may be compared against a cut-off value. A cut-off value is the value above which the test may be considered positive; that is, the analyte of interest is present in the fluid sample to some degree of statistical confidence. Below the cut-off value, the test is generally considered not positive—either the analyte of interest is not present or the inventive lateral flow assay did not detect its presence. While a cut-off may established based upon a directly measured value, such as the amount of analyte detected, the results may be more meaningful if reported on an indirect, or relative, scale.

A cut-off lateral flow assay is more desirable as the measurement separation between a negative value and a positive value increases. A negative value is the reported value on the continuous scale in the case where the analyte of interest is statistically not present. Conversely, a positive value is the reported value on the continuous scale in the case where the analyte of interest is statistically present. As these values converge, the likelihood reduces of being able to statistically tell positives and negatives apart.

Also desirable is a cut-off lateral flow with increased precision at the cut-off. When there is less variation at the chosen cut-off, it is more likely that a positive can be accurately considered a positive and a negative be accurately considered a negative.

Assay results may be mapped onto either a "relative," discussed above, or an "absolute" scale. Absolute scales are measured in actual physical units, such as number of copies of analyte per milliliter of fluid. Measurement in the absolute scale may be preferable in testing for certain diseases or conditions, such as tests for cancer markers. In such preferable embodiments, the result may be expressed in units, such as ng/ml. Accordingly, the control zones may have value assigned concentrations of control agent. In an extension of the relative measurement concept, the density of reflectance (DR) values of a series of standards of known analyte concentration may be measured and the intensities relative to the controls (RI values) calculated as previously described. The RI values may then be plotted against analyte concentration to construct a standard curve in which the RI values are assigned concentration values of the analyte of interest. The RI of a sample may then be read on this value assigned standard curve, yielding a result labeled in the desired units.

Where possible, it is desirable to employ a single agent as both the analyte binding agent and the control agent. In comparison to assays where the analyte binding agent and the control agent are separate agents, assays where a single agent is employed provide a wider measurement separation of negative and positive sample populations, together with increased precision at the cut-off.

Many circumstances may affect the absolute reactivity of lateral flow assays, including, but not limited to, manufacturing-derived variations, operator induced variations, environmentally induced variations and sample effects. With conventional lateral flow assays, any of these variations may act to repress or arguably enhance reactivity of one strip over another, resulting in possible false negative or false positive results. Not controlling for these or other variations may result in significant imprecision, non-reproducibility, lack of sensitivity and lack of specificity of the tests.

Lateral flow assays are also subject to a number of interferences which might affect the absolute amount of binding of either analyte binding agent or control agent to the test zones. Influencing factors may include: 1) variability in the release of the second analyte binding agent or the control agent from a conjugate pad, 2) device to device variation in the non-specific binding of the analyte binding population to the test strip, 3) variability in the movement of the analyte binding population through or along the test strip during the assay due to variation in the pore size of the test strip or membrane strip materials or non-specific aggregation of the analyte binding agent. Variability of absolute measurements of binding due to these or other factors may therefore be unacceptably high in conventional lateral flow assays.

These sorts of variabilities may be reduced by using a single agent which includes the second analyte binding agent and the control agent. Any portion of the lateral flow assay matrix that has been exposed to the control agent is more likely to have been exposed to the second analyte binding agent, as compared to conventional two-population assays. Any mechanism that impedes or prevents movement of the control agent along or through the lateral flow matrix is more likely to impede or prevent movement of the second analyte binding agent, as compared to conventional two-population assays. Third, the control agent may be chosen so as to reduce the amount of non-specific binding of the second analyte binding agent.

Reduction of non-specific binding may also occur due to modification of hydrophobicity/hydrophilicity profile of the analyte detection matrix. Reduction in aggregation "self-association" of the analyte detection matrix particles, which might hinder movement of matrix along the strip, may also be achieved by choosing a control agent with suitable properties. A final advantage is that, due to the need to prepare fewer reagents, manufacturing costs may be reduced.

Multiple control zones, as disclosed herein, offer a number of potential advantages in the practice of lateral flow assays. Additional control zones may be used to extend the dynamic range of the assay standard curve whether the curve is linear or nonlinear. Multiple control zones may also be used to define whether a prozone or high dose hook effect is present in a given assay. If such an effect is present, then the user can be advised to dilute the sample to unambiguously determine the concentration of the analyte in question

EXAMPLES

1. Construction of Test Strip

In this example, the construction of a test strip having a design as illustrated in FIGS. 1 and 7 is described. Backed sheets of Millipore SRHF nitrocellulose (4.8 cm×20 cm) (membrane strip 404) were coated by longitudinally dispensing one antigen band (test zone 410) and two control bands (test zones 412, 414) onto the nitrocellulose 404 using a Bio Dot XYZ3000 Dispensing platform with Biojets operating at a frequency of 120 Hz. 20.83 nl/drop and 0.5 ul/cm. The nitrocellulose sheets 404 were then dried for one hour at 37° C. in a forced air incubator, blocked for fifteen minutes in a solution of PBS containing 10 mg/ml BSA, 1% (w/v) PEG 8000, 3% (w/v) mannitol, 0.3% (w/v) gelatin, 0.01% (w/v) sodium azide and 0.05% (w/v) sodium dodecyl sulfate and then dried for an additional hour in a forced air incubator at 37° C. Coated nitrocellulose sheets 404 were stored desiccated at room temperature in foil pouches.

Gelman 8980 glass fiber pads for use as conjugate buffer pads 416 were preblocked by dipping in a solution of PBS 10 mg/ml BSA, 1% (w/v) Triton X-100, 2.5% (w/v) sucrose and 0.3% (w/v) polyvinylpyrrolidone K-30 and then drying for 2 hours in a forced air incubator. A conjugate solution in PBS 10 mg/ml BSA, 1% (w/v) Triton X-100, 2.5% (w/v) sucrose and 0.3% (w/v) polyvinylpyrrolidone was longitudinally dispensed on the preblocked conjugate buffer pads 416 using a Bio Dot XYZ3000 Dispensing platform with a single Biojet operating at a frequency of 120 Hz and delivering 104.17 nl/drop and 2.5 μL/cm. The conjugate buffer pads 416 were coated with conjugate in patterns of from two to six lines per cm with three patterns coated on each 3 cm×10 cm pad. Coated conjugate buffer pads 416 were vacuum dried at 2 Torr for two hours at room temperature and then cut into three 1 cm×20 cm sections each containing one pattern.

Test strips were prepared by affixing one 4.8 cm×20 cm backed nitrocellulose sheet 404, one 1 cm×20 cm coated conjugate buffer pad 416 and one 1.2 cm×20 cm Gelman Cytosep 1662 sheet 406 onto one adhesive coated 0.010" thick 6 cm×20 cm vinyl backing sheet 402 (G&L Precision Die Cutting). A 0.5 cm wide sample application pad 406 was affixed to the nitrocellulose 404 using double sided adhesive 409. Strips 0.5 cm wide were cut from the assembled sheet with a G&L Precision Die Cutting Drum Slitter. To assemble the test strip into a test cartridge (illustrated in FIG. 5A), the strip was placed in the bottom half of the holder, a 0.6 cm.×1.5 cm. absorbent pad 408 was placed over the top of the strip and the pins of the top half of the holder aligned with the holes of the bottom half and the holder tightly pressed together.

2. Analysis of Buffer Addition Time and Volume Dependence of Test Strips

Strips used in this example were constructed as described in Example 1. The strips were coated with 800 μg/ml Rabbit Anti-Dinitrophenyl (Anti-DNP) in the high control band (test zone 414), 200 μg/ml Rabbit Anti-Dinitrophenyl (Anti-DNP) in the low control band (test zone 412) and a solution of Herpes 2 $gG_2$ antigen having an optical density at 280 nm of approximately 0.115 in the test zone 410. The order of the bands on the strip was antigen band closest to the conjugate buffer pad, low control zone between the antigen band and the high control and the high control farthest from the conjugate buffer pad and closest to the absorbent pad.

The preblocked conjugate buffer pads 416 were coated with Protein A-OMNI™ conjugate [Protein A/BSA-DNP (2×/0.5×)]–8.5 nm gold by mixing three volumes of the stock conjugate solution (OD 520 approximately 63) with one volume PBS containing 40 mg/ml BSA, 4% (w/v) Triton X-100, 10% (w/v) sucrose and 1.2% (w/v) polyvinylpyrrolidone K-30 and 0.15 volumes 20×PBS. The mixture was dispensed onto the preblocked buffer conjugate buffer pads as described in Example 1.

The assay was carried out by placing the cassette on the lab bench and then adding either 32.5 μL, 35 μL, 40 μL, 45 μL or 50 μL of Herpes 2 moderate positive sample 705145 to the sample pad 406 through the sample addition port of the cassette. 125 μL of conjugate buffer (PBS, 10 mg/ml BSA, 0.1% sodium azide and 2 mM EDTA) was then added to conjugate buffer addition pad 416 at either 0 Min., 5 Min. or 15 Min. after the sample reached the terminal sample flow zone 116. The cassette containing the strip then was placed in a ReLIA™ machine set up to run and read the ReLIA™ assay for the detection of antibodies to Herpes 2. Strip temperature was set to 40° C. and the strips were read after 10 minutes.

As can be seen from the results shown in FIG. 8, the results from the ReLIA™ stop flow Herpes 2 assay were independent of both the sample volume added and the time of incubation before initiation of reverse flow for sample volumes from 35 to 45 μL and incubation times of up to fifteen minutes, the longest delay investigated. Within this range of volumes and incubation times, the CV on the assay result was 12.5%.

3. Herpes 2 Assay

Strips used in this example were coated with 800 μg/ml Rabbit Anti-Dinitrophenyl (Anti-DNP) in the high control band, 200 μg/ml Rabbit Anti-Dinitrophenyl (Anti-DNP) in the low control band and a solution of Herpes 2 $gG_2$ antigen having an optical density at 280 nm of approximately 0115 in the antigen band. The order of the bands on the strip was antigen band closest to the conjugate buffer pad, low control zone between the antigen band and the high control and the high control farthest from the conjugate buffer pad and closest to the absorbent pad. Nitrocellulose sheets were coated and strips prepared as described in Example 1.

Preblocked conjugate buffer pads were coated with Protein A-OMNI™ conjugate [Protein A/BSA-DNP (2×/0.5×)]–8.5 nm gold by mixing three volumes of the stock conjugate solution (OD 520 approximately 63) with one volume PBS containing 40 mg/ml BSA, 4% (w/v) Triton X-100, 10% (w/v) sucrose and 1.2% (w/v) polyvinylpyrrolidone K-30 and 0.15 volumes 20×PBS. The mixture was dispensed onto preblocked conjugate buffer pads as described in Example 1.

The assay was carried out by placing the cassette on the lab bench and then adding 40 μL of the Herpes 2 positive or negative samples noted in FIG. 9, to the sample pad through the sample addition port of the sample cassette. When the liquid front of the sample reached the terminal sample flow zone, the cassette containing the strip was placed in a ReLIA™ machine set up to run and read the ReLIA™ assay for the detection of antibodies to Herpes 2. At the prompt, 125 μL of conjugate buffer (PBS, 10 mg/ml BSA, 0.1% sodium azide and 2 mM EDTA) was added to the conjugate buffer port of the cassette. Strip temperature was set to 40° C. and the strips were read after 10 minutes. Relative intensity (RI) values of the samples were calculated according to an algorithm which assigns the assay low control response (density of reflectance) an RI of 1, the assay high control response (density of reflectance) an RI of 3 and zero response as an RI of 0.

As shown in FIG. 9, all Herpes 2 positive specimens gave relative intensity values (RI) of 0.58 or greater while all Herpes 2 negative samples gave RI values of 0.01 or lower, demonstrating that the positive and negative populations are well separated in this assay.

4. *Helicobacter Pylori* Assay

Strips used in this example were coated with 800 μg/ml Rabbit Anti-Dinitrophenyl (Anti-DNP) in the high control band, 200 μg/ml Rabbit Anti-Dinitrophenyl (Anti-DNP) in the low control band and a solution of *Helicobacter pylori* antigen having an optical density at 280 nm of approximately 1.157 in the antigen band. The order of the bands on the strip was antigen band closest to the conjugate buffer pad, low control zone between the antigen band and the high control and the high control farthest from the conjugate buffer pad and closest to the absorbent pad. Nitrocellulose sheets were coated and strips prepared as described in Example 1.

Preblocked conjugate buffer pads were coated with Protein A-OMNI™ conjugate [Protein A/BSA-DNP (2×/0.5×)]–8.5 nm gold by mixing three volumes of the stock conjugate solution (OD 520 approximately 63) with one volume PBS containing 40 mg/ml BSA, 4% (w/v) Triton X-100, 10% (w/v) sucrose and 1.2% (w/v) polyvinylpyrrolidone K-30 and 0.15 volumes 20×PBS. The mixture was dispensed onto preblocked conjugate buffer pads as described in Example 1.

The assay was carried out by placing the cassette on the lab bench and then adding 40 µL of the *Helicobacter pylori* positive or negative samples noted in FIG. 10, to the sample pad through the sample addition port of the sample cassette. When the liquid front of the sample reached the terminal sample flow zone, the cassette containing the strip was placed in a ReLIA™ machine set up to run and read the ReLIA™ assay for the detection of antibodies to *Helicobacter pylori*. At the prompt, 125 µL of conjugate buffer (PBS, 10 mg/ml BSA, 0.1% sodium azide and 2 mM EDTA) was added to the conjugate buffer port of the cassette. Strip temperature was set to 40° C. and the strips were read after 10 minutes. Relative intensity (RI) values of the samples were calculated according to an algorithm which assigns the assay low control response (density of reflectance) an RI of 1, the assay high control response (density of reflectance) an RI of 3 and zero response as an RI of 0.

As shown in FIG. 10 all *Helicobacter pylori* positive specimens gave relative intensity values (RI) of 1.64 or greater while all *Helicobacter pylori* negative samples gave RI values of 1.14 or lower, demonstrating that the positive and negative populations are well separated in this assay.

It will be apparent to those skilled in the art that various modifications and variations can be made in the apparatus and methods of the present invention without departing from the spirit or scope of the invention. Thus, it is intended that the present invention cover the modifications and variations of this invention provided they come within the scope of the appended claims and their equivalents. Additionally, the following examples are appended for the purpose of illustrating the claimed invention, and should not be construed so as to limit the scope of the claimed invention.

What is claimed is:

1. A test strip adapted to receive a sample and detect an analyte therein, the test strip comprising:
   a sample addition zone to which a sample may be added;
   an absorbent zone positioned in a first flow direction relative to the sample addition zone;
   one or more test zones positioned in a second, different, flow direction relative to the sample addition zone, at least one of the test zones including a first analyte binding agent immobilized therein which is capable of binding to the analyte to be detected; and
   a terminal sample flow zone positioned in the second flow direction relative to the sample addition zone and distal to the one or more test zones,
   the absorbent zone having an absorption capacity relative to the other zones of the test strip such that when a sample is added to the sample addition zone, the sample initially diffuses from the sample addition zone both in the first flow direction to the absorbent zone and in the second flow direction past the one or more test zones to a distal diffusion point within the terminal sample flow zone and then reverses flow, and diffuses in the first flow direction past the one or more test zones toward the absorbent zone.

2. The test strip according to claim 1 wherein the test strip is adapted to receive a sample within a predetermined volume range between about 10 and 250 µL.

3. The test strip according to claim 1 wherein the test strip is adapted to receive a sample within a predetermined volume range between about 20 and 100 µL.

4. The test strip according to claim 1 wherein the test strip is adapted to receive a sample within a predetermined volume range between about 30 and 50 µL.

5. The test strip according to claim 1 wherein the terminal sample flow zone has a length from a proximal end to a distal end of between about 3 and 10 mm.

6. The test strip according to claim 1 wherein the first analyte binding agent does not bind to components in the sample other than the analyte.

7. The test strip according to claim 1 wherein the first analyte binding agent is selected from the group consisting of antibodies, engineered proteins, peptides, haptens, lysates containing heterogeneous mixtures of antigens having analyte binding sites, ligands and receptors.

8. The test strip according to claim 1 wherein the test zones further include at least a first control zone with a control binding agent immobilized therein.

9. The test strip according to claim 1 wherein the test zones further include a first control zone with a control binding agent immobilized therein, and a second control zone with a same control binding agent immobilized therein as the first control zone, the first and second control zones containing a different amount of the control binding agent immobilized therein.

10. The test strip according to claim 1 wherein the test strip further includes a zone distal to the terminal sample flow zone which includes a second analyte binding agent which is capable of binding to the analyte and diffusing to the one or more test zones.

11. The test strip according to claim 10 wherein the second analyte binding agent is capable of binding to components in the sample other than the analyte.

12. The test strip according to claim 10 wherein the second analyte binding agent does not bind to components in the sample other than the analyte.

13. The test strip according to claim 10 wherein the second analyte binding agent is labeled with a detectable marker.

14. The test strip according to claim 10 wherein the second analyte binding agent is attached to a particle which is capable of diffusing to the one or more test zones.

15. The test strip of claim 1, wherein the test strip comprises a sample pad in the sample addition zone and a double-sided adhesive between the sample pad and the test strip.

* * * * *